United States Patent
Ergueta Tejerina et al.

(10) Patent No.: US 11,723,744 B2
(45) Date of Patent: Aug. 15, 2023

(54) SYSTEMS AND METHODS FOR CONTROLLING GRIP FORCE OF JAWS WHEN TRANSITIONING BETWEEN POSITION CONTROL MODE AND FORCE MODE

(71) Applicant: Verb Surgical Inc., Santa Clara, CA (US)

(72) Inventors: Edgar Ignacio Ergueta Tejerina, San Jose, CA (US); Alireza Hariri, Berkeley, CA (US)

(73) Assignee: Verb Surgical Inc., Santa Clara, CA (US)

( * ) Notice: Subject to any disclaimer, the term of this patent is extended or adjusted under 35 U.S.C. 154(b) by 291 days.

(21) Appl. No.: 17/039,948

(22) Filed: Sep. 30, 2020

(65) Prior Publication Data

US 2022/0096193 A1    Mar. 31, 2022

(51) Int. Cl.
*A61B 90/00* (2016.01)
*A61B 34/30* (2016.01)
(Continued)

(52) U.S. Cl.
CPC .............. *A61B 90/03* (2016.02); *A61B 34/30* (2016.02); *G16H 20/40* (2018.01); *G16H 40/63* (2018.01); *A61B 17/29* (2013.01); *A61B 34/37* (2016.02); *A61B 2017/00022* (2013.01); *A61B 2090/032* (2016.02); *A61B 2090/064* (2016.02); *A61B 2090/065* (2016.02); *A61B 2090/067* (2016.02)

(58) Field of Classification Search
CPC ... A61B 34/30; A61B 17/29; A61B 2090/065; G16H 20/40; G16H 40/63
USPC .......................................... 700/260; 606/205
See application file for complete search history.

(56) References Cited

U.S. PATENT DOCUMENTS

| 6,594,552 B1 * | 7/2003 | Nowlin | A61B 34/70 318/568.22 |
| 10,166,082 B1 | 1/2019 | Hariri et al. | |

(Continued)

FOREIGN PATENT DOCUMENTS

| JP | 2020-039898 | 3/2020 |
| KR | 10-2019-0084333 | 7/2019 |

OTHER PUBLICATIONS

Unpublished U.S. Appl. No. 16/814,412, filed Mar. 10, 2020.
(Continued)

*Primary Examiner* — Nathan J Jenness
(74) *Attorney, Agent, or Firm* — Aikin & Gallant, LLP

(57) ABSTRACT

Disclosed are systems and methods for achieving a smooth transition in the grip force when the wrist jaws transition between the position and force mode. In the position mode, the desired jaw angle is above a threshold corresponding to an angle at which both jaws are just simultaneously in contact with an object held between the jaws or, if there is no object, when the jaws begin to touch each other. A feedback loop may determine that the jaws are transitioning between the modes based on changes of the desired jaw angle. The feedback loop may analyze the commanded grip force and the measured grip force to determine whether to adjust the commanded grip force during the transition. If so, the feedback loop may adjust the commanded grip force to reduce changes in the measured grip force that is otherwise based on the desired jaw angle.

20 Claims, 17 Drawing Sheets

(51) Int. Cl.
  *G16H 40/63*   (2018.01)
  *G16H 20/40*   (2018.01)
  *A61B 34/37*   (2016.01)
  *A61B 17/00*   (2006.01)
  *A61B 17/29*   (2006.01)

(56) References Cited

U.S. PATENT DOCUMENTS

| | | |
|---|---|---|
| 10,357,247 B2 | 7/2019 | Shelton, IV et al. |
| 2012/0310256 A1* | 12/2012 | Brisson .................. A61B 34/77 606/130 |
| 2013/0103050 A1* | 4/2013 | Richmond ........... A61B 17/285 606/130 |
| 2013/0123780 A1 | 5/2013 | McKenna et al. |
| 2019/0201022 A1 | 7/2019 | Schoettgen et al. |

OTHER PUBLICATIONS

Unpublished U.S. Appl. No. 16/814,419, filed Mar. 10, 2020.
Unpublished U.S. Appl. No. 16/814,422, filed Mar. 10, 2020.
Unpublished U.S. Appl. No. 16/814,426, filed Mar. 10, 2020.
International Search Report and Written Opinion for International Application No. PCT/IB2021/057757 dated Nov. 23, 2021, 12 pages.

* cited by examiner

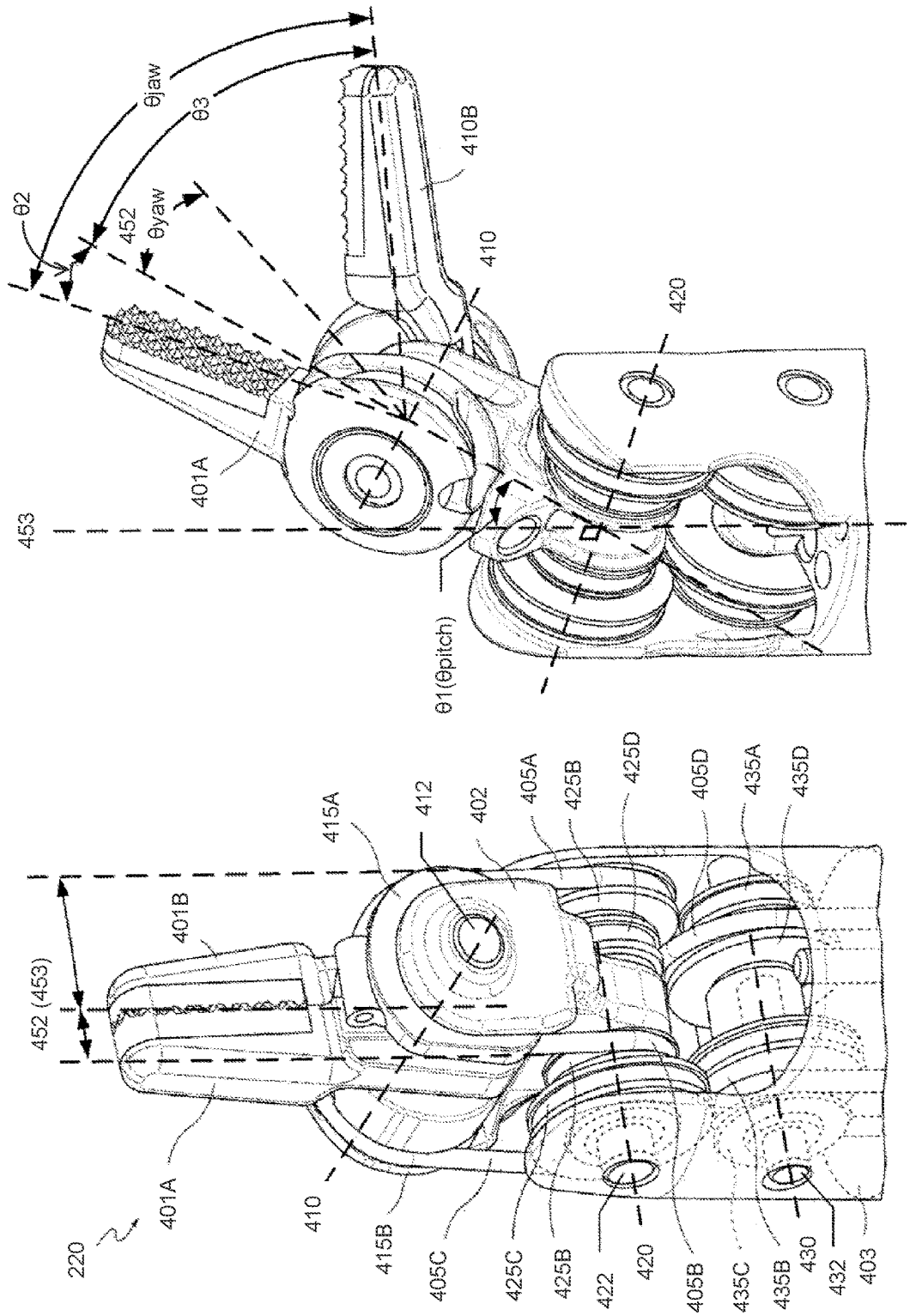

SYSTEMS AND METHODS FOR CONTROLLING GRIP FORCE OF JAWS WHEN TRANSITIONING BETWEEN POSITION CONTROL MODE AND FORCE MODE

TECHNICAL FIELD

The subject technology generally relates to robotics and surgical systems, and more specifically, to controlling the grip force or opening force of surgical tools such as wrist jaws of robotically-assisted surgical systems.

BACKGROUND

Minimally-invasive surgery, MIS, such as laparoscopic surgery, uses techniques that are intended to reduce tissue damage during a surgical procedure. Laparoscopic procedures typically call for creating a number of small incisions in the patient, e.g., in the abdomen, through which several surgical tools such as an endoscope, a scalpel, a grasper, and a needle, are then inserted into the patient. A gas is injected into the abdomen which insufflates the abdomen thereby providing more space around the tips of the tools, making it easier for the surgeon to see (via the endoscope) and manipulate tissue at the surgical site. MIS can also be performed using a robotic system in which the surgical tools are operatively attached to the distal ends of robotic arms, and a control system actuates the arm and its attached tool so that the latter mimics the movements and tool specific commands of a user input device (UID) as the latter is being manipulated by a surgeon in their hand.

Surgical tools may include a robotic wrist supporting a pair of opposing jaws. The wrist and the jaws may move in multiple degrees-of-freedom as controlled by commands from the remote operator to perform grasping, cutting, suturing, and other surgical tasks. For example, actuators in a tool drive of the robotic arm may drive multi-axial motions (e.g. pitch and yaw) of the wrist jaws to pivot, open, close the jaws, or to control the grip force or opening force between the jaws while moving the wrist to any angular position. The jaws may grasp patient tissue, hold a cutting instrument, etc. Precise control of the grip force or opening force when closing or opening the jaws is critical to prevent damage to the tissue or to ensure precision cutting by the instrument. In addition, the jaws may operate in a positional mode in which the angle between the pair of jaws are commanded to a desired jaw angle and a force mode in which the jaws are commanded to apply a desired grip force. A smooth transition between the positional mode and the force mode minimizes undesirable sudden changes in the grip force that may cause an accidental drop of any object being grasped.

SUMMARY

A system and method is disclosed for limiting the grip force generated by closing robotic wrist jaws while operating in a position control mode in which the jaws are commanded to a desired jaw angle prior to being commanded to generate a grip force. In the position control mode, or simply position mode, the desired jaw angle is above a threshold that corresponds to an angle at which both jaws are just simultaneously in contact with an object between the jaws or, if there is no object to grasp, when the jaws begin to touch each other. When the desired jaw angle is below the threshold, the wrist jaws are operating in a force control mode, or simply force mode, and the desired jaw angle is translated into a desired grip force. The disclosed system and method limits the maximum amount of grip force when the jaws are closing in the position mode to prevent damage to tissue that may be grasped by the jaws. The grip force may be estimated or measured. A feedback loop may analyze the desired jaw angle and the measured grip force to determine if the jaws are closing in the position mode and if the measured grip force exceeds a pre-specified maximum grip force threshold. If so, the feedback loop may calculate a grip force error to limit the measured grip force to the pre-specified maximum grip force threshold.

In another aspect, a system and method is disclosed for achieving a minimum jaw opening force by the wrist jaws when operating in the position mode. Maintaining a minimum jaw opening force while the jaws are opening in the position mode helps the jaws to overcome resistance that may be preventing the jaws from opening to the desired jaw angle. The opening force representing the jaw opening force and the jaw angle may be measured or estimated. A feedback loop may analyze the desired jaw angle, the estimated jaw angle, and the measured jaw opening force to determine if the jaws are opening in the position mode and if the measured jaw opening force is below a pre-specified minimum opening force threshold. If so, the feedback loop may calculate a jaw opening force error to maintain the jaw opening force above the pre-specified minimum opening force threshold.

In another aspect, a system and method is disclosed for achieving a smooth transition in the grip force when the wrist jaws transition between the position mode and the force mode. A smooth transition from the position mode to the force mode and vice versa minimizes undesired sudden changes in the grip force that may cause the wrist jaws to accidentally drop an object being grasped when the jaws traverse through the point of discontinuity between the two modes. In one embodiment, in order to transition from the position mode to the force mode, a debouncing strategy may be used to ensure that the desired jaw angle is smaller than the threshold between the position and force modes for a pre-specified minimum duration before the wrist jaws transition to the force mode.

In one embodiment, the system and method may determine the desired grip force from the desired jaw angle and may measure or estimate the grip force. A feedback loop may analyze the desired jaw angle, the desired grip force, and the measured grip force to determine if the jaws are transitioning from the position mode to the force mode, if an error between the measured grip force and the desired grip force is larger than a pre-specified maximum force error and if the desired grip force is increasing. If so, the feedback loop may set the desired grip force as the current measured grip force minus a pre-specified margin when the jaws transition from the position mode to the force mode.

In one embodiment, the feedback loop may analyze the desired jaw angle, the desired grip force as determined from the desired jaw angle, and the measured grip force to determine if the jaws are transitioning from the force mode to the position mode, if the desired grip force is smaller than a minimum grip force value, if the desired grip force is decreasing, and if the absolute value of the error between the measured grip force and the minimum grip force is smaller than a pre-specified maximum force error. If so, the feedback loop may set the desired grip force to the minimum grip force value when the jaws transition from the force mode to the position mode.

A method for controlling grip force generated by jaws of a gripper tool is disclosed. The method may include determining that the jaws are transitioning between the position mode and the force mode based on changes of a desired jaw angle between the jaws. During the position mode the jaws are driven with a commanded jaw angle, which may be the desired jaw angle. During the force mode, the jaws are driven with commanded grip force that is determined based on the desired jaw angle having a negative value. The method also includes determining based on the commanded grip force and the measured grip force whether to adjust the commanded grip force during the transition between the position mode and the force mode. If so, the method further includes adjusting the commanded grip force to reduce changes in the measured grip force that is otherwise determined based on the desired jaw angle during the transition.

BRIEF DESCRIPTION OF THE DRAWINGS

The accompanying drawings are provided together with the following description of various aspects and embodiments of the subject technology for a better comprehension of the invention. The drawings and the embodiments are illustrative of the invention, and are not intended to limit the scope of the invention. It is understood that a person of ordinary skill in the art may modify the drawings to generate drawings of other embodiments that would still fall within the scope of the invention.

FIGS. 4A and 4B are schematic diagrams illustrating the end effector of an exemplary grasper having a robotic wrist, a pair of opposing jaws, and a pulley and cable system for coupling the robotic wrist and the pair of jaws to the actuators of a tool drive, in accordance with aspects of the subject technology.

DETAILED DESCRIPTION

Figure 1:
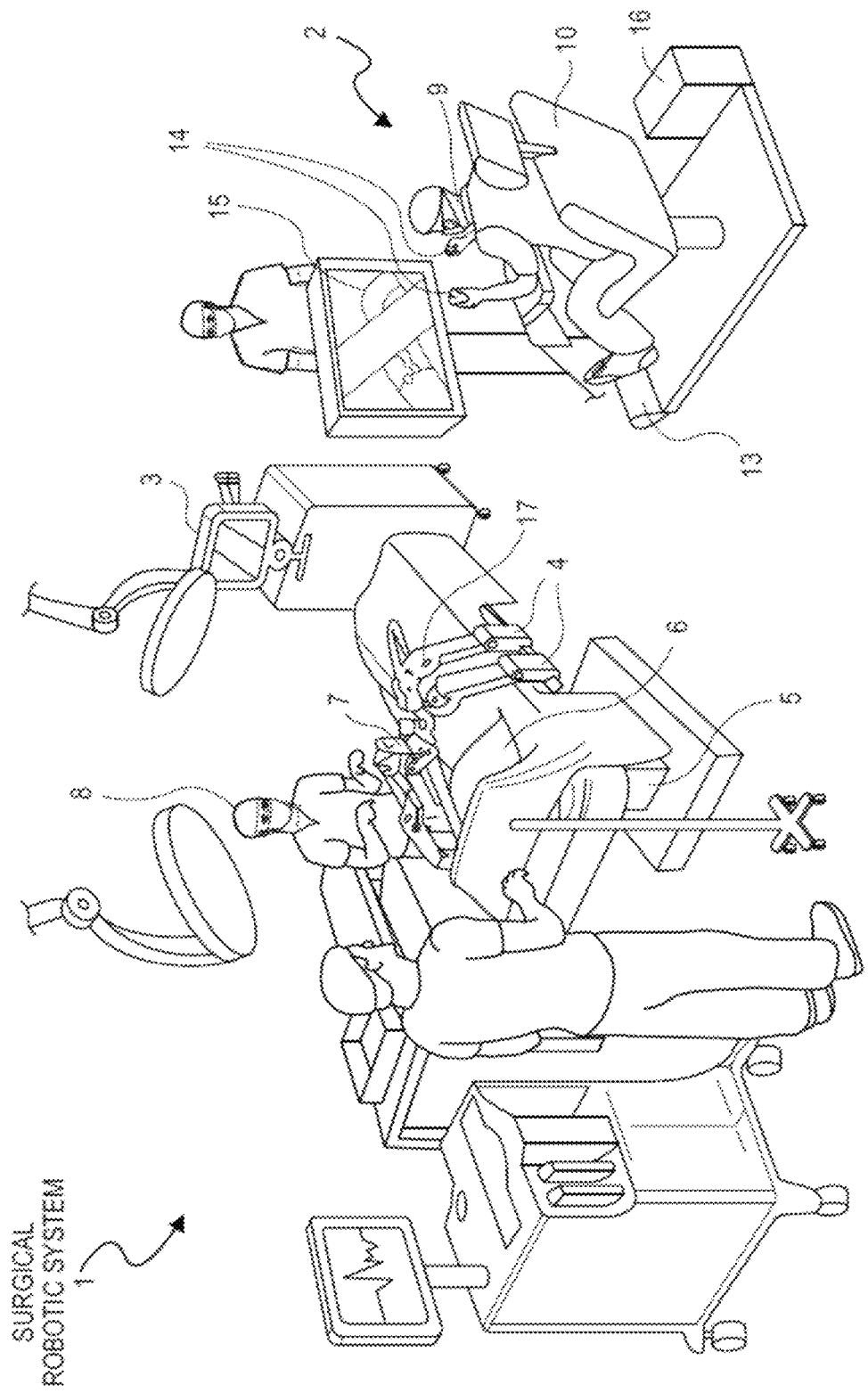
FIG. 1 is a pictorial view of an example surgical robotic system 1 in an operating arena, in accordance with aspects of the subject technology.

Examples of various aspects and variations of the subject technology are described herein and illustrated in the accompanying drawings. The following description is not intended to limit the invention to these embodiments, but rather to enable a person skilled in the art to make and use this invention.

Disclosed are feedback control systems and methods for controlling the grip force or opening force of end effectors of surgical robotic arms such as wrist jaws. Wrist jaws may be coupled to actuators of a tool drive through cables for effecting multi-axial motions of the wrist jaws. The feedback control system may command the wrist jaw to a pitch angle, a yaw angle, and a jaw angle between the jaws. When the commanded jaw angle is above a threshold, also referred to as a threshold for detent, the wrist jaws may operate in the position mode for moving the wrist jaws to a commanded position and orientation. The commanded jaw angle may also be referred to as the desired jaw angle. When the commanded jaw angle is below the threshold for detent, the wrist jaws may operate in the force mode from the position and orientation of the position mode and a desired grip force is generated by a grip force controller based on the commanded jaw angle. In one embodiment, the feedback control system may limit the maximum grip force when the jaws are closing in the position mode by analyzing the desired jaw angle and measuring or estimating the grip force as actually applied to determine if the measured grip force exceeds a pre-specified maximum grip force threshold. If so, the feedback control system may calculate a grip force error to adjust the grip force so that the measured grip force is limited to the pre-specified maximum grip force threshold.

In one embodiment, the feedback control system may maintain the minimum jaw opening force when the jaws are opening in the position mode. The feedback control system may measure or estimate the jaw angle as actually applied. The feedback control system may also measure or estimate the grip force or opening force of the jaws as actually applied. By analyzing the desired jaw angle, the measured jaw angle and the measured jaw opening force, the feedback control system may determine if the jaws are in the position mode, the difference between the desired jaw angle and the estimated jaw angle is larger than a threshold, and if the measured jaw opening force is smaller than a pre-specified minimum opening force threshold. If so, feedback control system may calculate an opening force error to adjust the grip force or opening force to maintain the measured jaw opening force above the pre-specified minimum opening force threshold.

In one embodiment, the feedback control system may use a debouncing algorithm to prevent the wrist jaws from oscillating between the position mode and the force mode when the jaw angle is set around detent. The feedback control system may determine if the desired jaw angle is smaller than the threshold for detent for a pre-specified duration. If so, the feedback control system may switch the wrist jaws from the position mode to the force mode. In one embodiment, the debouncing algorithm may be one-sided so that the wrist jaws may transition back to the position mode as soon as the desired jaw angle is larger than or equal to the threshold.

In one embodiment, the feedback control system may minimize undesired sudden changes in the grip force when transitioning between the position mode and the force mode. The grip force controller may calculate the current command for a desired grip force from the desired jaw angle. The feedback control system may measure or estimate the grip force as actually applied. The feedback control system may analyze the desired jaw angle, the desired grip force, and the measured grip force to determine if the jaws are transitioning from the position mode to the force mode and if an error between the measured grip force and the desired grip force is larger than a pre-specified maximum force error and if the desired grip force is increasing. If so, the feedback control system may set the grip force as the measured grip force minus a pre-specified margin when transitioning from the position mode to the force mode.

In one embodiment, the feedback control system may analyze the desired jaw angle, the desired grip force, and the measured grip force to determine if the jaws are transitioning from the force mode to the position mode, if the desired grip force is smaller than a pre-specified minimum grip force value, if the desired grip force is decreasing and if the absolute value of the error between the measured grip force and the minimum grip force is smaller than a pre-specified maximum force error. If so, the feedback control system may set the grip force to the pre-specified minimum grip force value when transitioning from the force mode to the position mode. In one embodiment, the pre-specified minimum grip force value may be set to 3N.

FIG. 1 is a pictorial view of an example surgical robotic system 1 in an operating arena, in accordance with aspects of the subject technology. The robotic system 1 includes a user console 2, a control tower 3, and one or more surgical robotic arms 4 at a surgical robotic platform 5, e.g., a table, a bed, etc. The arms 4 may be mounted to a table or bed on which the patient rests as shown in the example of FIG. 1, or they may be mounted to a cart separate from the table or bed. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In one aspect, the surgical tool 7 is a grasper such as wrist jaws that can grasp tissue of the patient. The surgical tool 7 may be configured to be controlled manually by a bedside operator 8, robotically via actuated movement of the surgical robotic arm 4 to which it is attached, or both. The robotic arms 4 are shown as being table-mounted but in other configurations the arms 4 may be mounted to a cart, the ceiling or a sidewall, or to another suitable structural support.

A remote operator 9, such as a surgeon or other human operator, may use the user console 2 to remotely manipulate the arms 4 and their attached surgical tools 7, e.g., referred to here as teleoperation. The user console 2 may be located in the same operating room as the rest of the system 1 as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 that are mounted on the distal ends of the arms 4.

In some variations, the bedside operator 8 may operate the system 1 in an "over the bed" mode in which the beside operator 8 (user) is at a side of the patient 6 and is simultaneously manipulating a robotically-driven tool (an end effector that is attached to the arm 4) with a handheld UID 14 held in one hand, and a manual laparoscopic tool in another hand. For example, the bedside operator's left hand may be manipulating the handheld UID to control a robotically-driven tool, while the bedside operator's right hand may be manipulating a manual laparoscopic tool. In this particular variation of the system 1, the bedside operator 8 can perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient.

An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, which opens or closes jaws of the grasper at a distal end of surgical tool 7 to grip tissue within patient 6.

In some aspects, the communication between the platform 5 and the user console 2 may be through a control tower 3, which may translate user commands that are received from the user console 2 (and more particularly from the console computer system 16) into robotic control commands that are transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output (video feed) may also be encrypted to ensure privacy and all or portions of the video output may be saved to a server or electronic healthcare record system.

Figure 2:
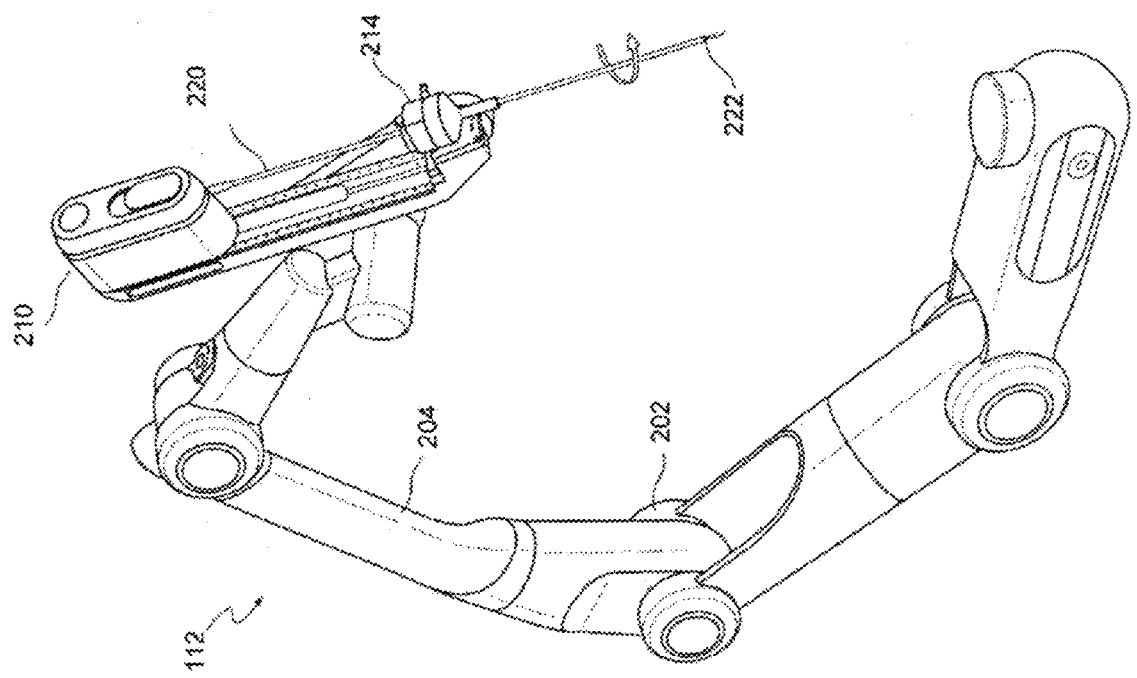
FIG. 2 is a schematic diagram illustrating one exemplary design of a robotic arm, a tool drive, and a cannula loaded with a robotic surgical tool, in accordance with aspects of the subject technology.

FIG. 2 is a schematic diagram illustrating one exemplary design of a robotic arm, a tool drive, and a cannula loaded with a robotic surgical tool, in accordance with aspects of the subject technology. As shown in FIG. 2, the example surgical robotic arm 112 may include a plurality of links (e.g., a link 202) and a plurality of actuated joint modules (e.g., a joint 204) for actuating the plurality of links relative to one another. The joint modules may include various types, such as a pitch joint or a roll joint, which may substantially constrain the movement of the adjacent links around certain axes relative to others. Also shown in the exemplary design of FIG. 2 is a tool drive 210 attached to the distal end of the robotic arm 112. The tool drive 210 may include a cannula 214 coupled to its end to receive and guide a surgical instrument 220 (e.g., endoscopes, staplers, etc.). The surgical instrument (or "tool") 220 may include an end effector 222 at the distal end of the tool. The plurality of the joint modules of the robotic arm 112 can be actuated to position and orient the tool drive 210, which actuates the end effector 222 for robotic surgeries.

Figure 3A:
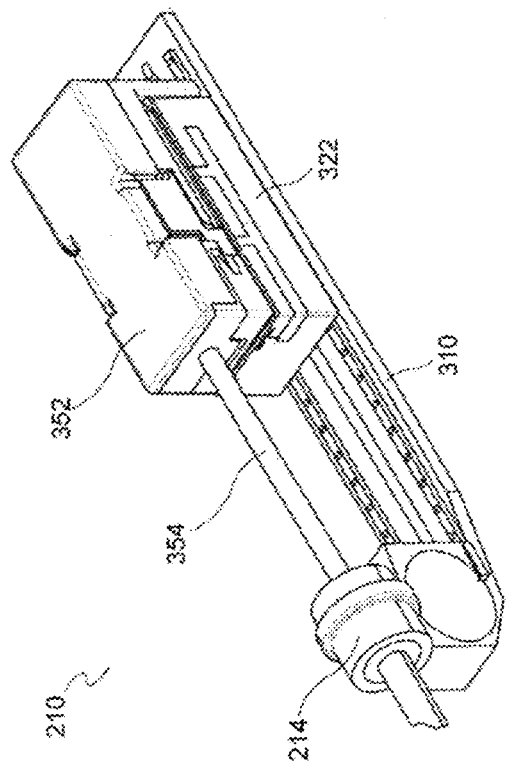
FIGS. 3A and 3B are schematic diagrams illustrating an exemplary tool drive with and without a loaded tool, respectively, in accordance with aspects of the subject technology.
Figure 3B:
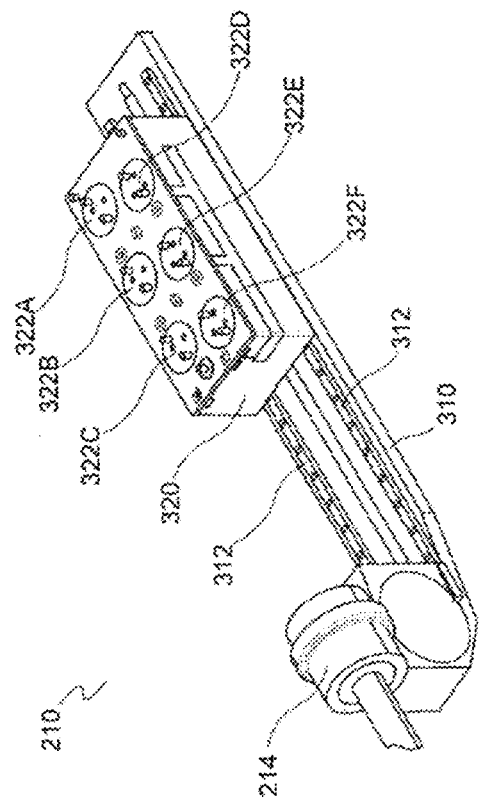

FIGS. 3A and 3B are schematic diagrams illustrating an exemplary tool drive with and without a loaded tool, respectively, in accordance with aspects of the subject technology. As shown in FIGS. 3A and 3B, in one variation, the tool drive 210 may include an elongated base (or "stage") 310 having longitudinal tracks 312 and a tool carriage 320, which is slidingly engaged with the longitudinal tracks 312. The stage 310 may be configured to couple to the distal end of a robotic arm such that articulation of the robotic arm may position and/or orient the tool drive 210 in space. Additionally, the tool carriage 320 may be configured to receive a tool base 352 of the tool 220, which may also include a tool shaft 354 extending from the tool base 352 and through the cannula 214, with the end effector 222 (not shown) disposed at the distal end.

Additionally, the tool carriage 320 may actuate a set of articulated movements of the end effector, such as through a cable system or wires manipulated and controlled by actuated drives (the terms "cable" and "wire" are used interchangeably throughout this application). The tool carriage 320 may include different configurations of actuated drives. For example, the rotary axis drives may include a motor with a hollow rotor and a planetary gear transmission at least partially disposed within the hollow rotor. The plurality of rotary axis drives may be arranged in any suitable manner. For example, the tool carriage 320 may include six rotary drives 322A-322F arranged in two rows, extending longitudinally along the base that are slightly staggered to reduce width of the carriage and increase the compact nature of the tool drive. As clearly shown in FIG. 3B, rotary drives 322A, 322B, and 322C may be generally arranged in a first row, while rotary drives 322D, 322E, and 322F may be generally arranged in a second row that is slightly longitudinally offset from the first row.

FIGS. 4A and 4B are schematic diagrams illustrating the end effector of an exemplary grasper having a robotic wrist, a pair of opposing jaws, and a pulley and cable system for coupling the robotic wrist and the pair of jaws to the actuators of a tool drive, in accordance with aspects of the subject technology. Note that although the following tool model and controller design are described with reference to the exemplary surgical robotic grasper, the proposed control system for position and grip force control may be adapted to any tools that include an end effector coupled to a tool shaft via a robotic wrist, which allows multi-axial motion (e.g., pitch and yaw) of the end effector. Similar tools include, but not limited to, graspers, grippers, forceps, needle drivers, retractors, and cautery instruments.

As shown in FIG. 4A, the pair of opposing jaws 401A and 401B are movably coupled to a first yoke 402 of the robotic wrist via an extended axle 412 along a first axis 410. The first yoke 402 may be movably coupled to a second yoke 403 of the robotic wrist via a second extended axle 422 along a second axis 420. The pair of jaws 401A and 401B may each be coupled or integrally formed with pulleys 415A and 415B respectively, via the extended axle 412, so that both jaws can rotate about the axis 410. Pulleys 425A, 425B, 425C and 425D are coupled to the extended axle 422 and rotate around the axis 420. The pulleys 425A, 425B, 425C and 425D are arranged into a first set of pulleys 425B and 425C on one side of the yoke 402 and a second set of pulleys 425A and 425D on the other side of the yoke 402. The pulleys 425A and 425C are outer pulleys and the pulleys 425B and 425D are inner pulleys. Similarly, the third set of pulleys 435A, 435B, 435C and 435D are coupled to a third extended axle 432 and rotate around the axis 430, which is parallel to the axis 420.

The grasper 220 can be actuated to move one or both of the jaws 401A and 401B in a variety of ways around the axis 410. For example, the jaws 401A and 401B may open and close relative to each other. The jaws 401A and 401B may also be actuated to rotate together as a pair to provide a yaw motion of the grasper 220. In addition, the first yoke 402, the pulleys 415A and 415B, and the jaws 401A and 401B can rotate about the axis 420 to provide a pitch motion of the grasper 220. The motion of the robotic wrist and/or the jaws of the tool can be actuated by controlling four independent cables 405A-405D. As shown in FIG. 4A, cable 405A may start (or terminates) from one side of the pulley 415A and route along pulleys 425A and 435A, and cable 405B is configured to terminate at the other side of the pulleys 415A and route through pulleys 425B and 435B. Similarly, another pair of cables 405C and 405D can be coupled to the jaw 401B. For example, cable 405C extends from one side of the pulley 415B to pulleys 425C and 435C; and cable 405D routes through pulleys 425D and 435D and terminates at the other side of pulley 415B. The third set of pulleys 435A, 435B, 435C and 435D are arranged in such away as to keep the cables 405A-405D affixing to the second set of pulleys 425A-425D and prevent the cables from slipping or sliding relative to the pulleys 425A-425D.

As shown in FIGS. 4A and 4B, the grasper 220 can be actuated to move the jaws 401A and 401B in a variety of ways such as grasping (e.g., jaws rotating independently about axis 410), yaw (e.g., jaws rotating together about axis 410), and pitch (e.g., jaws rotating about axis 420) by imparting motion to one or more of the pulleys 415A, 415B, 425A, 425B, 425C, and 425D to thereby impart motion on the first yoke 402 and/or one or both of the jaws 401A and 401B. Cables 405A-405D can be grouped into two antagonistic pairs, that is, when one cable of the antagonistic pair is actuated or tensioned, while the other cable is loosened, the jaw will rotate in one direction. Whereas when only the other cable is tensioned, the jaw will rotate in an opposite direction.

For example, cables 405A and 405B are the first antagonistic pair for moving jaw 401A, and cables 405C and 405D are the second antagonistic pair for controlling jaw 401B. When cable 405A is tensioned (e.g., by at least one of the rotary drives 322a-322f) while cable 405B is loosened, jaw 401A closes (moving towards the opposite jaw 401B). On the other hand, when cable 405B is tensioned and cable 405A is loosened, jaw 401A opens (moving away from the opposite jaw 401B). Similarly, when tensioned, cable 405C closes jaw 401B (moving towards the opposite jaw 401A) and cable 405D opens jaw 401B (moving away from the opposite jaw 401A) while the other cable loosens. As another example, grip force between the jaw 401A and jaw 401B can be achieved by continuing to tension both cable 405A and cable 405C (while cable 405B and cable 405D are loosened) after the jaws are closed (touching each other).

In case when both cables of an antagonistic pair are tensioned at the same time while both cables of the other pair are loosened, the pulley 415A or pulley 415B do not rotate. Instead, the first yoke 402 together with the jaws 401A and 401B are imparted by the pulleys 415A and 415B to pitch about the axis 420. For example, when the pair of cables 405A and 405B are both tensioned simultaneously while the pair of cable 405C and 405D are loosened, the jaws (together with the yoke 402) pitch out of the plane of the paper. Whereas when both cables 405C and 405D are tensioned simultaneously and the pair 405A and 405B are kept loose, the jaws pitch into the plane of the paper.

FIG. 4B is a schematic diagram illustrating example angle definitions for various motions of the grasper 220, in accordance with aspects of the subject technology. The angles are defined in reference to axes 410 and 420, as well as an axis 452 of the first yoke 402 and an axis 453 of the second yoke 403. For example, as shown in FIG. 4B, an angle ($\theta_1$) between axis 452 and the axis 453 may represent the rotation angle of the yoke 402 around axis 420, which may also be defined as the pitch angle ($\theta_{pitch}$) of the grasper 220 (while in FIG. 4A, the axis 452 of the yoke 402 is superimposed over the axis 453 of the yoke 403 because the jaws are staying in the reference position, i.e., no pitch motions). In addition, angles ($\theta_2$) and ($\theta_3$) can represent the angles between each of the jaws 401A and 401B and the axis 452 of the yoke 402 (as the origin), respectively. To differentiate the sides of the axis 452, angles ($\theta_2$) and ($\theta_3$) may take on different signs. For example, angle ($\theta_2$) is negative and angle ($\theta_3$) is positive, as illustrated in FIG. 4B.

In order to perform control tasks, it is often beneficial to define a consistent coordinate frame for the joint angles. For example, we may further define the jaw angle ($\theta_{jaw}$) as the angle between the two jaws 401A and 401B, and the yaw angle ($\theta_{yaw}$) as the angle between the axis 452 and the line bisecting the jaw angle. As mentioned, pitch angle ($\theta_{pitch}$) may be defined as angle ($\theta_1$) between axis 452 and the axis 453. Therefore:

$$\begin{cases} \theta_{yaw} = \frac{1}{2}(\theta_2 + \theta_3) \\ \theta_{jaw} = (\theta_3 - \theta_2) \\ \theta_{pitch} = \theta_1 \end{cases} \quad \text{Equation 1}$$

Described below is a method and system for controlling angular position and grip force of a distal end effector of a robotic surgical instrument. The end effector may include a robotic wrist and a pair of opposing members (e.g., jaws or claws), each being movable between an open position and a closed position actuated by two antagonistic wires. A total of four wires may each be driven by an independent actuator or motor, as illustrated in FIGS. 3 and 4. The control system may include feedback loops involving position and velocity feedback from the actuators and force feedback measured on the four wires, to effect desired position and grip force. In some implementations, the actuator controllers may be running a position plus feedforward current mode. For example, a position controller in the position mode may drive the distal end effector to the desired angular position in space based on the positional feedback, while in the force mode a grip force controller provides additional feedforward current based on the grip force measured by load cells on the four wires to achieve the desired grip force between the opposing members.

Figure 5:
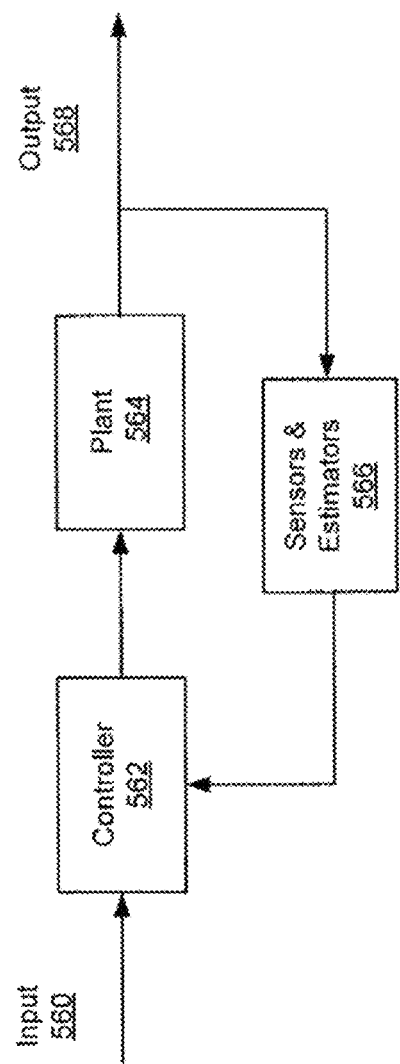
FIG. 5 is a block diagram of an exemplary control system for controlling the position and grip force of an end effector of a robotic surgical tool, in accordance with aspects of the subject technology.

FIG. 5 is a block diagram illustrating a high-level control system for controlling a surgical tool, in accordance with aspects of the subject technology. The control system comprises an input 560, a controller 562, a plant 564, an output 568, and sensors and estimators 566 on a feedback path between the output 568 and the controller 562. The plant 564 may include tool actuators and end effector (e.g., rotary drives 322A-322F of FIG. 3B and cables 405A-405D of wrist jaws of FIG. 4A; see also actuator units 510 and cable and wrist links 512 in FIG. 10). The controller 562 may include one or more processors configured by software instructions stored on a memory to calculate motions of the plant 564 in response to the input 560, which may indicate a desired movement of the surgical tool's end effector, such as the desired $\theta_{pitch}$, desired $\theta_{yaw}$, and desired $\theta_{jaw}$ of the wrist jaws of FIG. 4B. Commands thus generated by the controller 562 may drive the tool actuators to facilitate the desired movement of the end effector. In one embodiment, the desired $\theta_{pitch}$, $\theta_{yaw}$, and $\theta_{jaw}$ may be generated by the UID 14 under the control of the remote operator 9 of FIG. 1. The output 568, such as position, velocity, cable tension, and grip force or opening force of the end effector, may be directly measured or estimated by the sensors and estimators 566 and fed back to the controller 562 for closed-loop control.

In one embodiment, when the desired jaw angle $\theta_{jaw}$ of the wrist jaws is greater than or equal to a threshold, the desired $\theta_{jaw}$, which is also referred to as the commanded $\theta_{jaw}$, may be treated as a position control command in the position mode. The threshold is used to determine detent, and may correspond to an angle at which both jaws are just simultaneously in contact with the object(s) in between. In case there are no objects to grasp, the threshold is zero degree when the jaws begin to touch each other. In the position mode, the controller 562 may translate the desired $\theta_{jaw}$, as well as the desired $\theta_{pitch}$ and desired $\theta_{yaw}$, into corresponding actuator position commands to drive the wrist jaws to the desired position and orientation. When the desired $\theta_{jaw}$ is below the threshold, the wrist jaws are operating in a force control mode, or simply force mode, and the desired jaw angle is translated into a desired grip force command. The controller 562 may generate a current command in addition to the position command to achieve the desired grip force.

In one embodiment, the controller 562 may limit the maximum amount of grip force when the jaws are closing in the position mode to prevent damage to tissue that may be grasped by the jaws. The grip force of the jaws may be estimated or measured by the sensors and estimators 566. The controller 562 may analyze the desired $\theta_{jaw}$ and the measured grip force to determine if the jaws are closing in the position mode and if the measured grip force exceeds a pre-specified maximum grip force threshold. If so, the controller 562 may calculate a grip force error to limit the measured grip force to the pre-specified maximum grip force threshold. For example, to determine if the jaws are closing in the position mode, the controller 562 may first verify that the desired $\theta_{jaw}$ is greater than or equal to the threshold for detent, and thus in the position mode, for more than a pre-specified duration. The controller 562 may employ a debouncing technique to verify that the desired $\theta_{jaw}$ has been decreasing for a pre-specified length of time. In one embodiment if the desired $\theta_{jaw}$ are sampled at a periodic frequency, the controller 562 may verify that the samples of the desired $\theta_{jaw}$ have been decreasing for a pre-specified number of samples.

To determine if the measured grip force exceeds a pre-specified maximum grip force threshold, the controller 562 may also employ a debouncing technique. In one embodiment, the feedback control loop of the control system of FIG. 5 may operate with a loop cycle time. A grip force counter may increase by one count for every control loop cycle during which the measured grip force is less than the maximum grip force threshold minus a margin. In one embodiment, the grip force counter may stop incrementing after it reaches a maximum count. When the measured grip force is larger than the maximum grip force threshold, the grip force counter may reset. The debouncing technique may declare that the measured grip force exceeds the maximum grip force threshold for an entirety of a window that spans a number of loop cycles equaling to the grip force counter when the measured grip force is larger than the maximum grip force minus the margin anywhere within the window.

As an example, assume the measured grip force is initially below the maximum grip force threshold minus the margin and the grip force counter is incrementing. When the measured grip force increases beyond the maximum grip force threshold, the grip force counter may be reset. The feedback control loop of the controller 562 may attempt to change the actuator position commands to drive the wrist jaws to limit the measured grip force to the maximum grip force threshold. However, even if the measured grip force drops below the maximum grip force threshold but stays above the maximum grip force threshold minus the margin, the feedback control loop may still consider the measured grip force to be larger than the maximum grip force threshold so as to limit the maximum measured grip force. Assume the measured grip force dips below the maximum grip force threshold minus the margin for only a few loop cycles but then increases above this level again. The grip force counter may increment to the number of loop cycles that the measured grip force was briefly below the maximum grip force threshold minus the margin. As long as the measured grip force stays above the maximum grip force threshold minus the margin within a window that spans a number of loop cycles equaling to the grip force counter (e.g., the number of loop cycles that the measured grip force dipped briefly below the maximum grip force threshold minus the margin), the feedback control loop may still consider the measured grip force to be larger than the maximum grip force threshold for the entire duration of the window so as to limit the maximum measured grip force.

When the controller 562 determines that the jaws are closing in the position mode and that the measured grip force exceeds the maximum grip force threshold, the controller may limit the measured grip force to the maximum grip force threshold. In one embodiment, the controller 562 may calculate a grip force error that is the difference between the maximum grip force threshold and the measured grip force. A zero steady-state type controller, such as a proportional plus integral (PI) force controller, may be deployed to receive the grip force error to maintain or limit the measured grip force at the maximum grip force threshold. The output of the PI force controller may be combined with the output of the inverse kinematic matrix that operates on errors in the desired position and orientation of the wrist jaws to generate compensated actuator position commands. The compensated actuator position commands are added to the existing actuator position commands to drive the wrist jaws to limit the maximum amount of grip force when the jaws are closing in the position mode at the desired position and orientation.

Figure 6A:
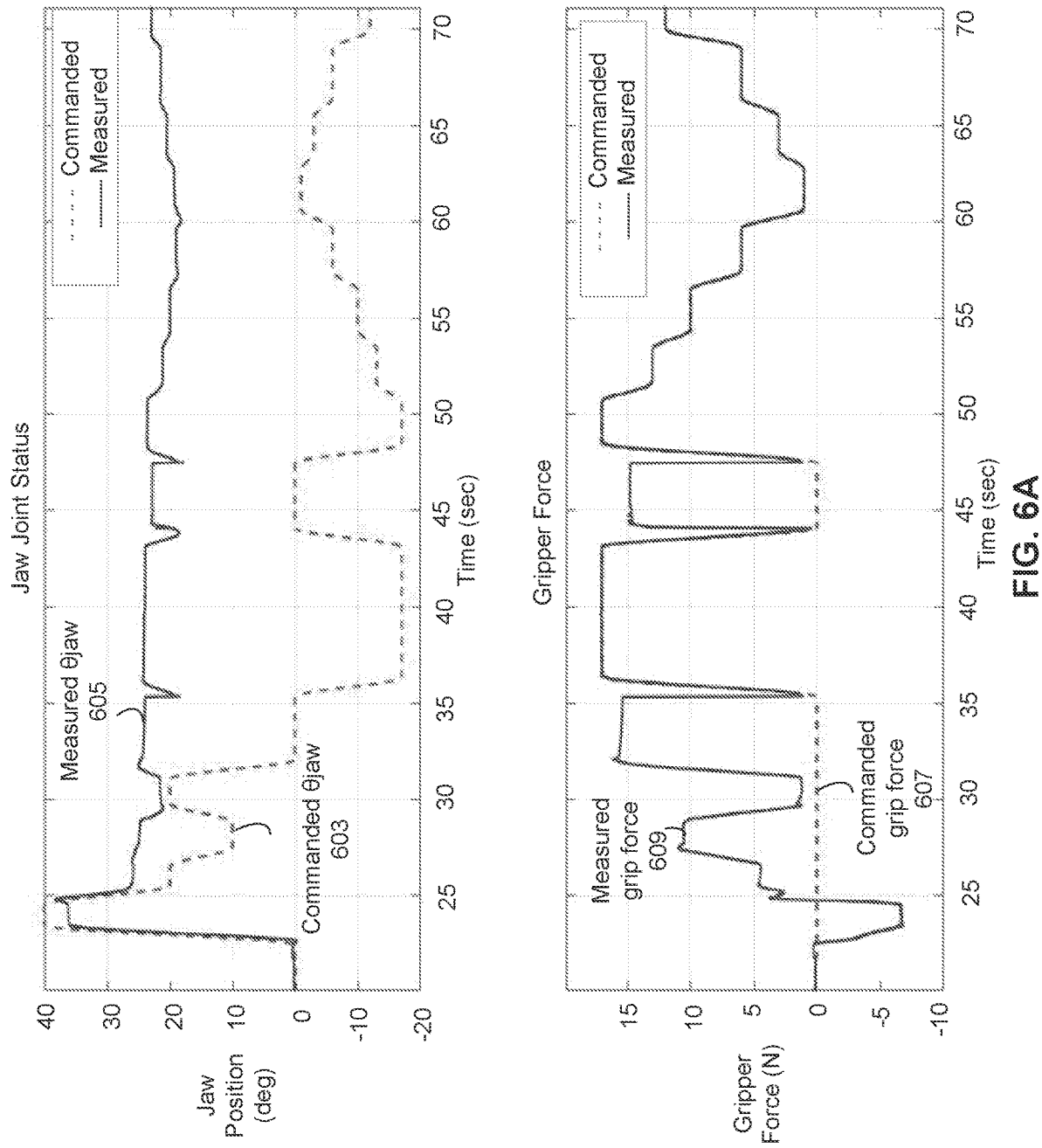
FIG. 6A is a time plot showing the commanded jaw angle, the measured jaw angle, the commanded grip force, and the measured grip force of the wrist jaws when the measured grip force is not limited while the jaws are closing in the position mode.

FIG. 6A is a time plot showing the commanded $\theta_{jaw}$ 603, the measured $\theta_{jaw}$ 605, the commanded grip force 607, and the measured grip force 609 of the wrist jaws when the measured grip force 609 is not limited while the jaws are closing in the position mode. The threshold $\theta_{jaw}$ between the position mode and the force mode is set at zero so that when the commanded $\theta_{jaw}$ 603 is greater than or equal to zero degree, the wrist jaws are operating in the position mode. When the commanded $\theta_{jaw}$ 603 is less than zero degree, the wrist jaws are operating in the force mode.

FIG. 6A shows that from 20 to 35 second and again from 44 to 47 second, the wrist jaws are operating in the position mode. The measured $\theta_{jaw}$ 605 stays within a relatively narrow range even as the commanded $\theta_{jaw}$ 603 changes within the position mode or within the force mode, presumably because the jaws are grasping an object. During the position mode, the commanded grip force 607, which is the desired grip force, may be set to a default value of zero N because the wrist jaws are not operating in the force mode. However, the measured grip force 609 may be much larger. For example, from 26 to 28 second and from 31 to 35 second, when the jaws are closing in the position mode or are held in the closed position, the measured grip force 609 exceeds 10 N and may go as high as 15 N because the measured grip force is not limited. In the force mode (e.g., 35-44 second and after 47 sec), the grip force controller may set the commanded grip force 607 as a function of the commanded $\theta_{jaw}$ 603 and the feedback control loop may keep the measured grip force 609 to be the same as the commanded grip force 607.

Figure 6B:
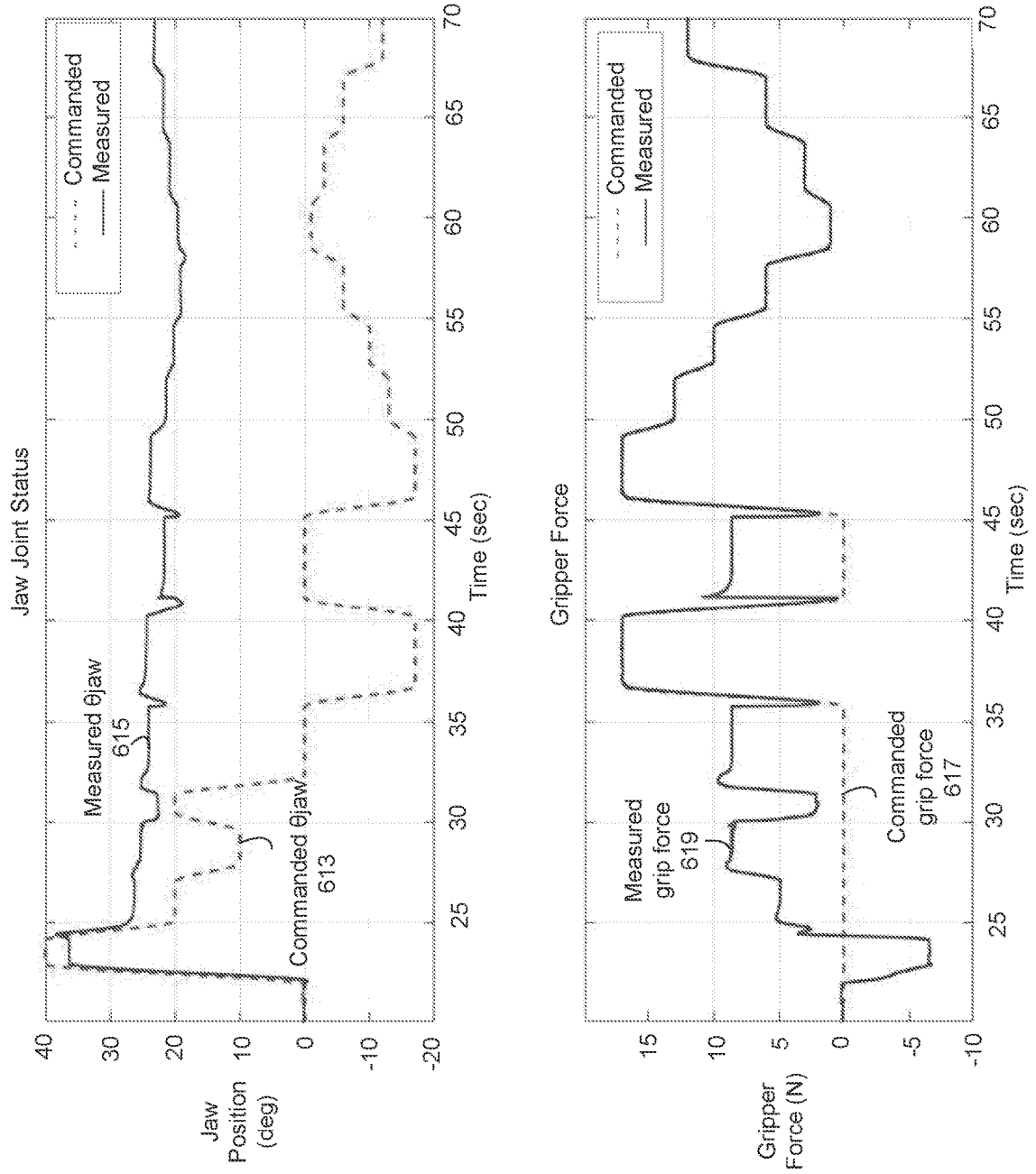
FIG. 6B is a time plot showing the commanded jaw angle, the measured jaw angle, the commanded grip force, and the measured grip force of the wrist jaws when a control system limits the measured grip force to a pre-specified maximum threshold during jaw closing in the position mode, in accordance with aspects of the subject technology.

FIG. 6B is a time plot showing the commanded $\theta_{jaw}$ 613, the measured $\theta_{jaw}$ 615, the commanded grip force 617, and the measured grip force 619 of the wrist jaws when a control system limits the measured grip force to a pre-specified maximum grip force threshold during jaw closing in the position mode, in accordance with aspects of the subject technology. The maximum grip force threshold is set to 8.5 N.

In FIG. 6B, the time plot of the commanded $\theta_{jaw}$ 613 and the measured $\theta_{jaw}$ 615 is the same as the command $\theta_{jaw}$ 603 and the measured $\theta_{jaw}$ 605 of FIG. 6A when the measured grip force is not limited. During the position mode, the commanded grip force 617 is again set by the grip force controller to the default value of zero N. However, the measured grip force 619 is limited by the grip force controller to the maximum grip force threshold of 8.5 N during the position mode when the jaws are closing or are held in the closed position (e.g., 27-30 second, 32-36 sec, and 41-45 sec). Note that the limit on the maximum grip force in the position mode has no effect on the force mode. Thus, in the force mode, the measured grip force 619 may be allowed to exceed the maximum grip force threshold of 8.5 N by following the commanded grip force 617.

Figure 7:
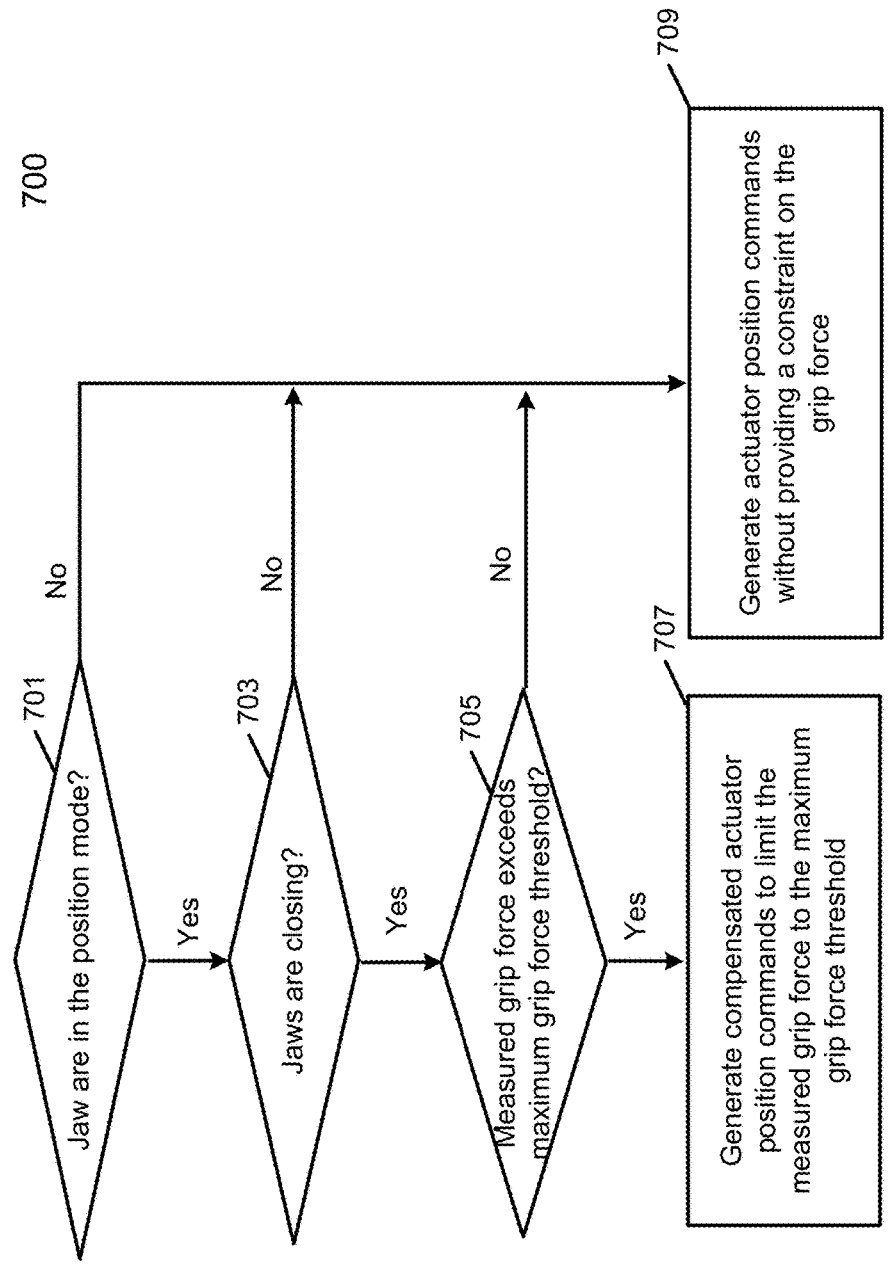
FIG. 7 is a flow chart illustrating a method for feedback control of a surgical robotic system to limit the grip force of the wrist jaws to a pre-specified maximum threshold during jaws closing in the position mode by analyzing the desired jaw angle and the measured grip force, in accordance with aspects of the subject technology.

FIG. 7 is a flow chart illustrating a method 700 for feedback control of a surgical robotic system to limit the grip force of the wrist jaws to a pre-specified maximum threshold during jaws closing in the position mode by analyzing the desired jaw angle and the measured grip force, in accordance with aspects of the subject technology. The method 700 may be implemented by the controller 562 of the control system of FIG. 5 that receives the desired $\theta_{jaw}$ from user input and the measured grip force from sensors and estimators 566 to generate actuator position commands for driving the wrist jaws.

In block 701, the method 700 determines if the wrist jaws are in the position mode. In one embodiment, block 701 may determine if the desired $\theta_{jaw}$ is greater than or equal to the threshold $\theta_{jaw}$ between the position mode and the force mode for more than a pre-specified time period to confirm that the wrist jaws are in the position mode. In one embodiment, the threshold $\theta_{jaw}$ may be set to zero. If the wrist jaws are not in the position mode, the wrist jaws are in the force mode and the grip force is not limited. In block 709, the method 700 generates actuator position commands without placing a constraint on the grip force. In one embodiment, block 709 translates the desired $\theta_{jaw}$ into a desired grip force command to achieve the desired grip force in addition to generating the actuator position commands.

If the jaws are in the position mode, block 703 determines if the jaws are closing. In one embodiment, block 703 may employ a debouncing technique to determine if the desired $\theta_{jaw}$ has been decreasing for a pre-specified duration or for a pre-specified number of samples. In one embodiment, the jaws may be considered closing if the desired $\theta_{jaw}$ is held at a quiescent state without increasing. If the jaws are not closing, the grip force is not limited even in the position mode. The method 700 defaults to block 709 to generate actuator position commands without placing a constraint on the grip force.

If the jaws are closing in the position mode, block 705 determines if the measured grip force exceeds a pre-specified maximum grip force threshold. In one embodiment, block 705 may employ a debouncing technique to determine if the measured grip force is larger than the maximum grip force threshold minus a margin anywhere within a window that spans a number of samples equaling to a grip force counter. In one embodiment, the measured grip force may be sampled at a loop cycle time of the feedback control system of FIG. 5. The grip force counter may increment by one for every control loop cycle during which the measured grip force is less than the maximum grip force threshold minus the margin. When the measured grip force is larger than the maximum grip force threshold, the grip force counter may reset. As long as the measured grip force exceeds the maximum grip force threshold minus the margin anywhere within the window that spans the number of samples equaling to the grip force counter, the measured grip force is considered to exceed the maximum grip force threshold for the entire window. Otherwise, the measured grip force does not exceed the maximum grip force threshold and the method 700 defaults to block 709 to generate actuator position commands without placing a constraint on the grip force.

If the measured grip force exceeds the maximum grip force threshold while the jaws are closing in the position mode, block 707 generates compensated actuator position commands to limit the measured grip force to the maximum grip force threshold. In one embodiment, block 707 may calculate a grip force error that is the difference between the maximum grip force threshold and the measured grip force. A zero steady-state type controller, such as a proportional plus integral (PI) force controller, may receive the grip force error to generate a compensated grip force command. The output of the PI force controller may be combined with the output of the inverse kinematic matrix that operates on errors in the desired position and orientation of the wrist jaws to generate the compensated actuator position commands. The compensated actuator position commands may be added to existing actuator position commands to drive the wrist jaws so as to limit the measured grip force to the maximum grip force threshold.

In another aspect, the controller 562 may maintain a minimum jaw opening force by the wrist jaws when operating in the position mode. The minimum jaw opening force may also be referred to as the minimum grip force. Maintaining a minimum jaw opening force while the jaws are opening in the position mode helps the jaws to overcome resistance that may be preventing the jaws from opening to the desired jaw angle. The jaw angle and the opening force of the jaws may be estimated or measured by the sensors and estimators 566. The controller 562 may analyze the desired $\theta_{jaw}$, the estimated $\theta_{jaw}$, and the measured opening force to determine if the jaws are opening in the position mode, if the jaw angle error between the desired $\theta_{jaw}$ and the estimated $\theta_{jaw}$ is larger than a threshold, and if the measured opening force is below a pre-specified minimum jaw opening force threshold. If so, the controller 562 may calculate an opening force error between the pre-specified minimum jaw opening force threshold and the measured opening force to maintain the measured opening force above the pre-specified minimum jaw opening force threshold.

In one embodiment, to determine if the jaws are opening in the position mode, the controller 562 may first verify that the desired $\theta_{jaw}$ is greater than or equal to the threshold for detent, and thus in the position mode, for more than a pre-specified duration. The controller 562 may then determine if the opening jaws in the position mode are meeting resistance that prevents the jaws from opening to the desired $\theta_{jaw}$. In one embodiment, the controller 562 may employ a debouncing technique to verify that the desired $\theta_{jaw}$ is larger than the estimated $\theta_{jaw}$ and that the $\theta_{jaw}$ error, which is the difference between the desired $\theta_{jaw}$ and the estimated $\theta_{jaw}$, is larger than an $\theta_{jaw}$ error threshold for a pre-specified length of time. In one embodiment if the desired $\theta_{jaw}$ and the estimated $\theta_{jaw}$ are sampled at a periodic frequency, the controller 562 may verify that the $\theta_{jaw}$ error is larger than the $\theta_{jaw}$ error threshold for a pre-specified number of samples.

To determine if the measured opening force is below the pre-specified minimum jaw opening force threshold, the controller 562 may also employ a debouncing technique. A jaw opening force counter may increase by one count for every control loop cycle during which the measured opening force is larger than the minimum jaw opening force threshold plus a margin. In one embodiment, the jaw opening force counter may stop incrementing after it reaches a maximum count. When the measured opening force is less than the minimum jaw opening force threshold, the jaw opening force counter may reset. The debouncing technique may declare that the measured opening force is below the minimum jaw opening force threshold for an entirety of a window that spans a number of loop cycles equaling to the jaw opening force counter when the measured opening force is less than the minimum jaw opening force threshold plus the margin anywhere within the window.

As an example, assume the measured opening force is initially above the minimum jaw opening force threshold plus the margin and the jaw opening force counter is incrementing. When the measured opening force drops below the minimum jaw opening force threshold, the jaw opening force counter may be reset. The feedback control loop of the controller 562 may attempt to change the actuator position commands to drive the wrist jaws to maintain the measured opening force above the minimum jaw opening force threshold. However, even if the measured opening force increases above the minimum jaw opening force threshold but stays below the minimum jaw opening force threshold plus the margin, the feedback control loop may still consider the measured opening force to be smaller than the minimum jaw opening force threshold so as to maintain the minimum jaw opening force. Assume the measured opening force rises above the minimum jaw opening force threshold plus the margin for only a few loop cycles but then dips below this level again. The jaw opening force counter may increment to the number of loop cycles that the measured opening force was briefly above the minimum jaw opening force threshold plus the margin. As long as the measured opening force stays below the minimum jaw opening force threshold plus the margin within a window that spans a number of loop cycles equaling to the jaw opening force counter (e.g., the number of loop cycles that the measured opening force was briefly above the minimum jaw opening force threshold plus the margin), the feedback control loop may still consider the measured opening force to be smaller than the minimum jaw opening force threshold for the entire duration of the window so as to maintain the minimum jaw opening force.

When the controller 562 determines that the jaws are opening in the position mode, the $\theta_{jaw}$ error is larger than the $\theta_{jaw}$ error threshold, and the measured opening force is below the pre-specified minimum jaw opening force threshold, the controller may maintain the measured opening force above the minimum jaw opening force threshold. In one embodiment, the controller 562 may calculate a jaw opening force error that is the difference between the minimum jaw opening force threshold and the measured opening force. A zero steady-state type controller, such as a proportional plus integral (PI) force controller, may be deployed to receive the jaw opening force error to maintain the measured opening force at or above the minimum jaw opening force threshold. The output of the PI force controller may be combined with the output of the inverse kinematic matrix that operates on errors in the desired position and orientation of the wrist jaws to generate compensated actuator position commands. The compensated actuator position commands are added to the existing actuator position commands to drive the wrist jaws to maintain the minimum amount of opening force when the jaws are opening in the position mode at the desired position and orientation.

Figure 8A:
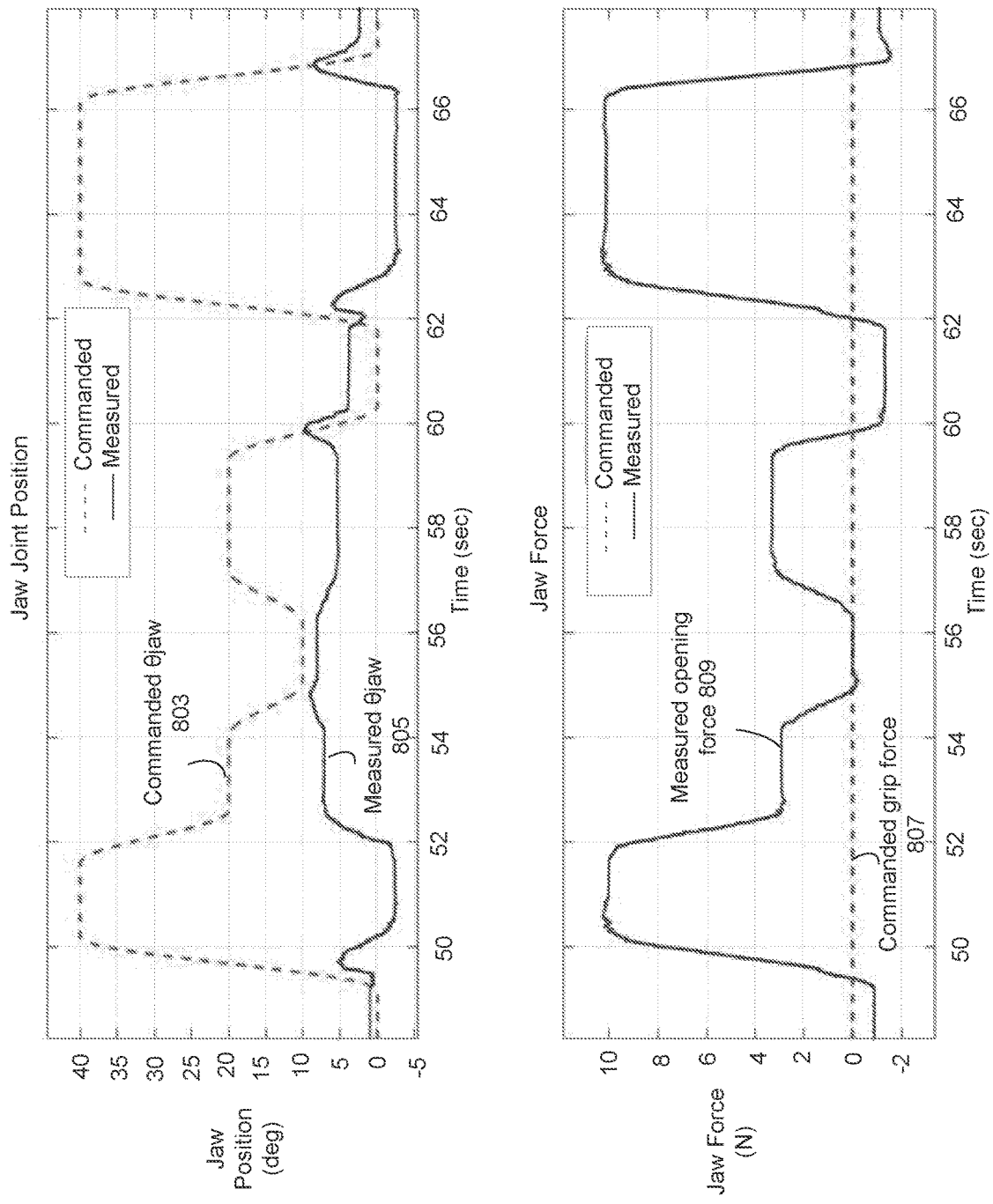
FIG. 8A is a time plot showing the commanded jaw angle, the measured jaw angle, the commanded grip force, and the measured opening force of the wrist jaws when the measured opening force is not maintained above a minimum level while the jaws are opening in the position mode.

FIG. 8A is a time plot showing the commanded $\theta_{jaw}$ 803, the measured $\theta_{jaw}$ 805, the commanded grip force 807, and the measured opening force 809 of the wrist jaws when the measured opening force 809 is not maintained above a minimum level while the jaws are opening in the position mode. The threshold $\theta_{jaw}$ between the position mode and the force mode, is set at zero so that when the commanded $\theta_{jaw}$ 603 is greater than or equal to zero degree, the wrist jaws are operating in the position mode. When the commanded $\theta_{jaw}$ 603 is less than zero degree, the wrist jaws are operating in the force mode. The $\theta_{jaw}$ error threshold is set at 5 degrees and the minimum opening force threshold is set at 4.4 N.

FIG. 8A shows that from 49 to 60 second and from 62 to 67 second, the wrist jaws are operating in the position mode. The measured $\theta_{jaw}$ 805 stays within a relatively narrow range even as the commanded $\theta_{jaw}$ 803 configures the jaw to close or open within the position mode, presumably because the opening jaws in the position mode are meeting resistance or are constrained from opening fully to the commanded $\theta_{jaw}$ 803. From 49-52 second, 56-59 second, and 62-66 second when the jaws are opening in the position mode or are maintained in the same $\theta_{jaw}$, the $\theta_{jaw}$ error, the difference between the larger commanded $\theta_{jaw}$ 803 and the smaller measured $\theta_{jaw}$ 805, may be larger than the $\theta_{jaw}$ error threshold of 5 degrees.

During the position mode, the commanded grip force 807 may be set by a grip force controller to a default value of zero N. Even during the force mode, the commanded grip force 807 is still set to zero N. A positive value for the measured opening force 809 corresponds to the opening force of the jaws in the position mode and a negative value corresponds to the grip force in the force mode when the jaws are closed. The measured opening force 809 in the position mode generally follows the profile of the commanded $\theta_{jaw}$ 803 because the jaws are constrained from opening to the commanded $\theta_{jaw}$ 803. The result is stronger measured opening force 809 when the commanded $\theta_{jaw}$ 803 is increased for wider opening of the jaws and conversely weaker measured opening force 809 when the commanded $\theta_{jaw}$ 803 is decreased for narrower opening of the jaws. Because the feedback control loop is not enabled to maintain the measured opening force 809 above the minimum opening force threshold of 4.4 N, between 53 to 60 second, the measured opening force 809 may drop below the minimum opening force threshold.

Figure 8B:
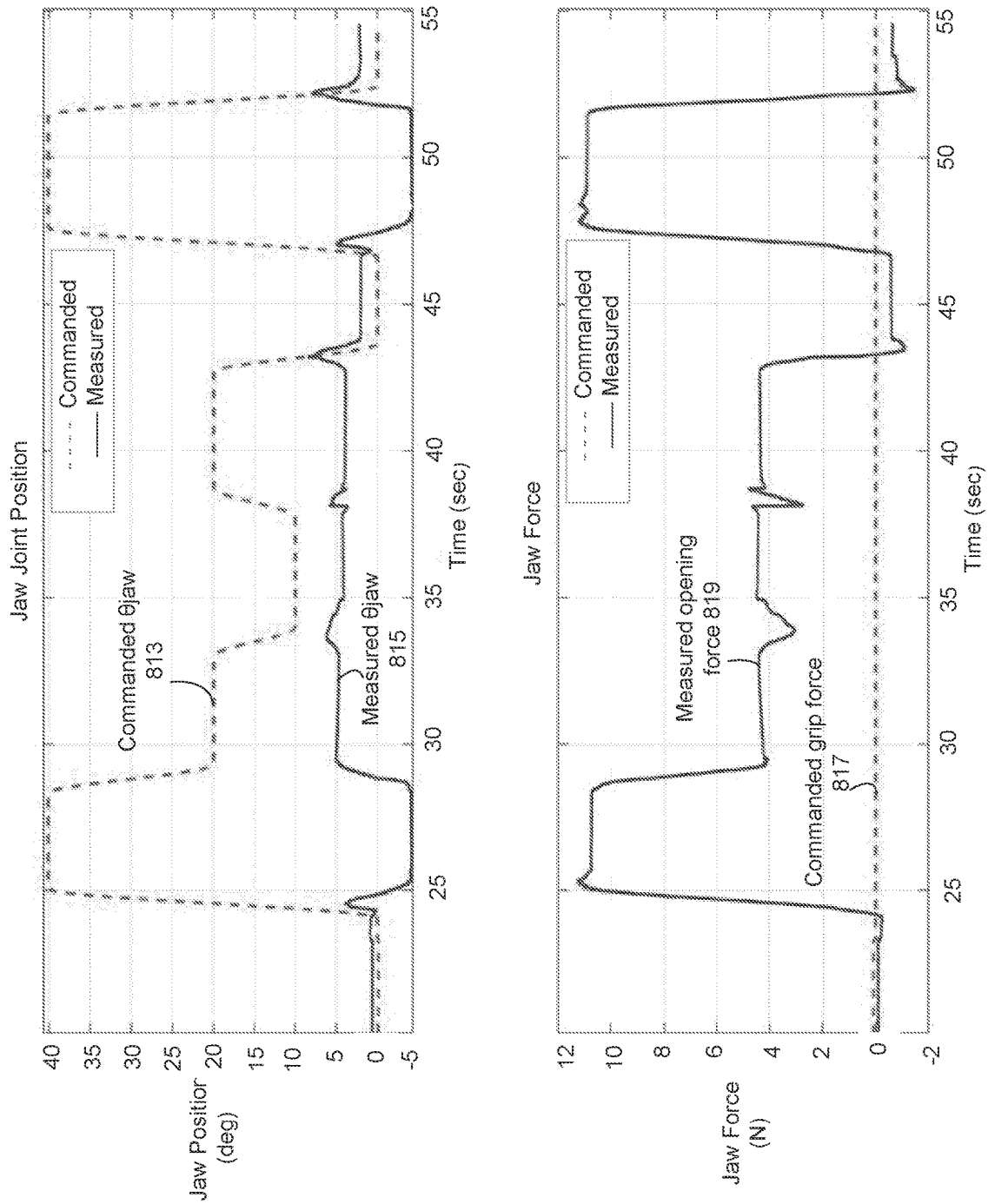
FIG. 8B is a time plot showing the commanded jaw angle, the measured jaw angle, the commanded grip force, and the measured opening force of the wrist jaws when a control system maintains the measured opening force above a pre-specified minimum opening force threshold during jaws opening in the position mode, in accordance with aspects of the subject technology.

FIG. 8B is a time plot showing the commanded $\theta_{jaw}$ 813, the measured $\theta_{jaw}$ 815, the commanded grip force 817, and the measured opening force 819 of the wrist jaws when a control system maintains the measured opening force 819 above a pre-specified minimum opening force threshold during jaws opening in the position mode, in accordance with aspects of the subject technology. The $\theta_{jaw}$ error threshold is again set at 5 degrees and the minimum opening force threshold is set at 4.4 N.

In FIG. 8B, the time plot of the commanded $\theta_{jaw}$ 813 and the measured $\theta_{jaw}$ 815 is generally the same as the commanded $\theta_{jaw}$ 803 and the measured $\theta_{jaw}$ 805 of FIG. 8A when the minimum jaw opening force is not maintained. During the position mode, the commanded grip force 817 is again set by the grip force controller to the default value of zero N. However, the measured opening force 819 is maintained by the feedback control loop and the grip force controller at or above the minimum opening force threshold of 4.4 N during the position mode between 30-43 second when the $\theta_{jaw}$ error, the difference between the larger commanded $\theta_{jaw}$ 813 and the smaller measured $\theta_{jaw}$ 815, is larger than the $\theta_{jaw}$ error threshold of 5 degrees. In particular, when the jaws are opening, maintaining the same $\theta_{jaw}$, or even closing in the position mode, the minimum measured opening force 819 is maintained. Note that minimum opening force threshold in the position mode has no effect on the force mode when the measured opening force 819 may be negative.

Figure 9:
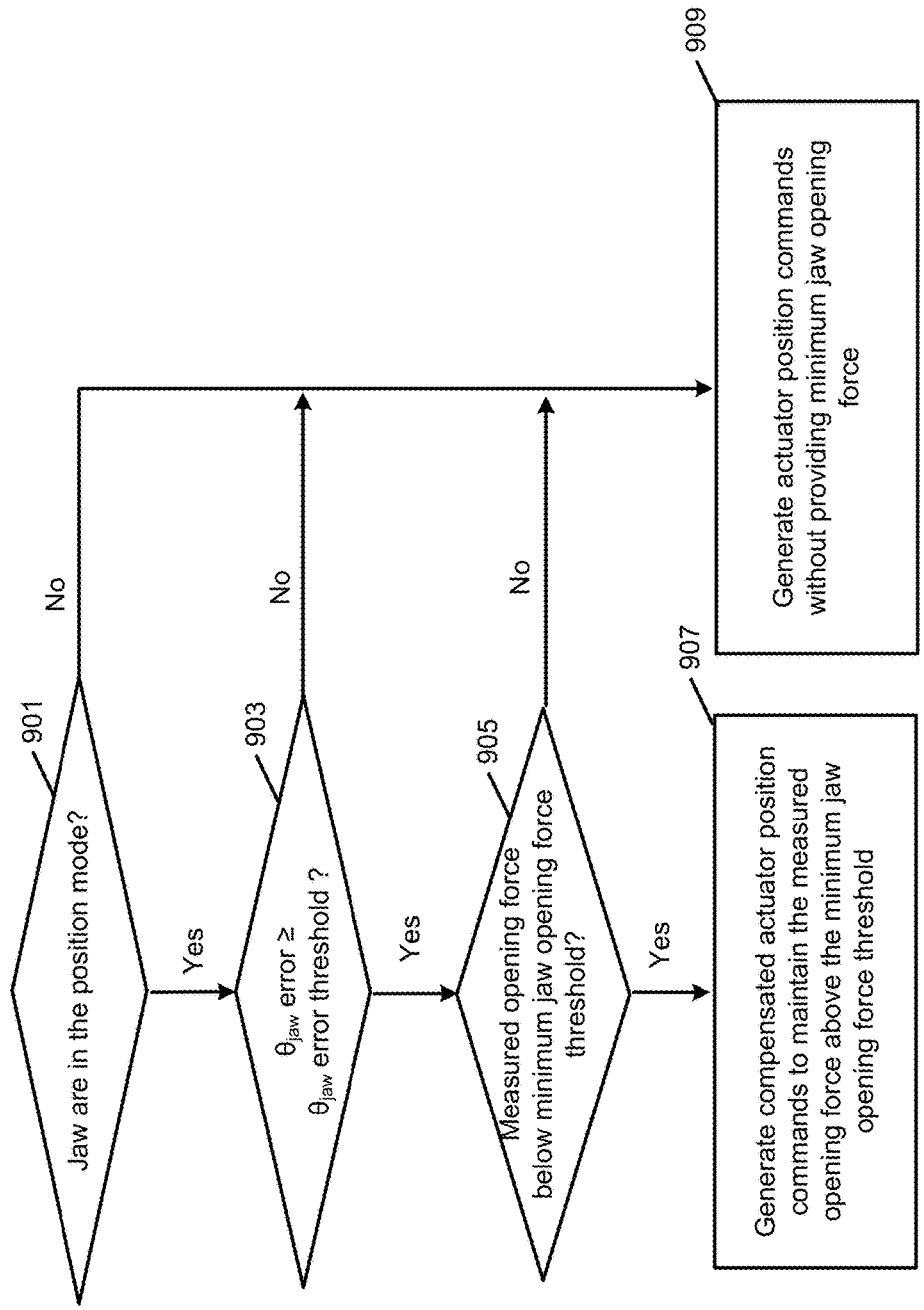
FIG. 9 is a flow chart illustrating a method for feedback control of a surgical robotic system to maintain the opening force of the wrist jaws above a pre-specified minimum opening force threshold during jaws opening in the position mode by analyzing the desired jaw angle, the estimated jaw angle and the measured opening force, in accordance with aspects of the subject technology.

FIG. 9 is a flow chart illustrating a method 900 for feedback control of a surgical robotic system to maintain the opening force of the wrist jaws above a pre-specified minimum jaw opening force threshold during jaws opening in the position mode by analyzing the desired jaw angle, the estimated jaw angle and the measured opening force, in accordance with aspects of the subject technology. The method 900 may be implemented by the controller 562 of the control system of FIG. 5 that receives the desired $\theta_{jaw}$ from user input, the estimated or the measured $\theta_{jaw}$, and the measured opening force from sensors and estimators 566 to generate actuator position commands for driving the wrist jaws.

In block 901, the method 900 determines if the wrist jaws are in the position mode. In one embodiment, block 901 may determine if the desired $\theta_{jaw}$ is greater than or equal to the threshold $\theta_{jaw}$ between the position mode and the force mode for more than a pre-specified time period to confirm that the wrist jaws are in the position mode. In one embodiment, the threshold $\theta_{jaw}$ may be set to zero. If the wrist jaws are not in the position mode, the wrist jaws are in the force mode and minimum opening force is not enabled. In block 909, the method 900 generates actuator position commands without maintaining a minimum opening force. In one embodiment, block 909 translates the desired $\theta_{jaw}$ into a desired grip force command to achieve the desired grip force or opening force in addition to generating the actuator position commands.

If the jaws are in the position mode, block 903 determine if the jaws are prevented from opening to the desired $\theta_{jaw}$ by determining if the $\theta_{jaw}$ error, which is the difference between the desired $\theta_{jaw}$ and the estimated or measured $\theta_{jaw}$, is larger than or equal to an $\theta_{jaw}$ error threshold. In one embodiment, block 903 may employ a debouncing technique to determine if the desired $\theta_{jaw}$ is larger than the estimated $\theta_{jaw}$ and that the $\theta_{jaw}$ error is larger than or equal to the $\theta_{jaw}$ error threshold for a pre-specified length of time. In one embodiment, block 903 may detect that the jaws are opening, maintaining a quiescent $\theta_{jaw}$, or closing by determining that the desired $\theta_{jaw}$ is increasing, staying the same, or decreasing, respectively. If the $\theta_{jaw}$ error is smaller than the $\theta_{jaw}$ error threshold, the method 900 defaults to block 909 to generate actuator position commands without maintaining a minimum opening force.

If the $\theta_{jaw}$ error is larger than or equal to the $\theta_{jaw}$ error threshold when the jaws are in the position mode, block 905 determines if the measured opening force is below a pre-specified minimum jaw opening force threshold. In one embodiment, block 905 may employ a debouncing technique to determine that the measured opening force is less than the minimum jaw opening force threshold plus a margin anywhere within a window that spans a number of samples equaling to a jaw opening force counter. In one embodiment, the measured opening force may be sampled at a loop cycle time of the feedback control system of FIG. 5. The jaw opening force counter may increment by one for every control loop cycle during which the measured opening force is larger than the minimum jaw opening force threshold plus the margin. When the measured opening force is less than the minimum jaw opening force threshold, the jaw opening force counter may reset. As long as the measured opening force is less than the minimum jaw opening force threshold plus the margin anywhere within the window that spans the number of samples equaling to the jaw opening force counter, the measured opening force is considered to be below the minimum jaw opening force threshold for the entire window. Otherwise, the measured opening force is more than or equal to the minimum jaw opening force threshold and the method 900 defaults to block 909 to generate actuator position commands without maintaining a minimum opening force.

If the measured opening force is less than the minimum jaw opening force threshold and the $\theta_{jaw}$ error is larger than or equal to the $\theta_{jaw}$ error threshold when the jaws are in the position mode, block 907 generates compensated actuator position commands to maintain the measured opening force above the minimum jaw opening force threshold. In one embodiment, block 907 may calculate a jaw opening force error that is the difference between the minimum jaw opening force threshold and the measured opening force. A zero steady-state type controller, such as a proportional plus integral (PI) force controller, may be deployed to receive the jaw opening force error to maintain the measured opening force at or above the minimum jaw opening force threshold. The output of the PI force controller may be combined with the output of the inverse kinematic matrix that operates on errors in the desired position and orientation of the wrist jaws to generate compensated actuator position commands. The compensated actuator position commands are added to the existing actuator position commands to drive the wrist jaws to maintain the minimum amount of opening force when the jaws are opening in the position mode.

In another aspect, the controller 562 may adjust the commanded grip force to smooth the grip force applied when the wrist jaws transition between the position mode and the force mode. Smoothing the grip force applied during mode transitions minimizes undesired sudden changes in the grip force caused by changes in the position and commanded grip force of the jaws that may cause the jaws to accidentally drop an object being grasped when the jaws traverse through the point of discontinuity between the two modes. During the position mode the desired $\theta_{jaw}$ is greater than or equal to the threshold for detent. A position controller may translate the desired $\theta_{jaw}$, as well as the desired $\theta_{pitch}$ and desired $\theta_{yaw}$, into corresponding actuator position commands to drive the wrist jaws to the desired position and orientation. During the force mode when the desired $\theta_{jaw}$ is below the threshold for detent, for example when the desired $\theta_{jaw}$ is negative for detent set at zero degree, a grip force controller may be enabled to interpret the desired $\theta_{jaw}$ as a grip force command and may translate the desired $\theta_{jaw}$ into compensation current that may be added to current for the existing position commands to drive the wrist jaws to achieve the commanded grip force.

In one embodiment, to smooth the grip force applied during mode transitions, a feedback control system may employ a debouncing technique when detent is set at zero degree. The debouncing technique may prevent the grip force controller from repeatedly getting enabled and disabled to create oscillation in the commanded grip force when the desired $\theta_{jaw}$ oscillates around positive and negative values.

In one embodiment, the feedback control system may minimize sudden changes in the grip force when the wrist jaws transition from the position mode to the force mode by analyzing the desired $\theta_{jaw}$, the commanded grip force, and the measured grip force. The feedback control system may determine if the commanded grip force is increasing due to the grip force controller getting enabled as indicated by the desired $\theta_{jaw}$ decreasing below the threshold for detent, and if an error between the measured grip force and the commanded grip force is larger than a pre-specified maximum force error. If so, the feedback control system may set the commanded grip force as the measured grip force minus a pre-specified margin when the wrist jaws transition from the position mode to the force mode.

In one embodiment, the feedback control system may minimize sudden changes in the grip force when the wrist jaws transition from the force mode to the position mode by analyzing the desired $\theta_{jaw}$, the commanded grip force, and the measured grip force. The feedback control system may determine if the commanded grip force is smaller than a pre-specified minimum grip force value, if the commanded grip force is decreasing due to the grip force controller being disabled as indicated by the desired $\theta_{jaw}$ increasing above the threshold for detent, and if the absolute value of an error between the measured grip force and the minimum grip force is smaller than a pre-specified maximum grip force error value. If so, the feedback control system may set the commanded grip force to the pre-specified minimum grip force value when the wrist jaws transition from the force mode to the position mode.

Figure 10:
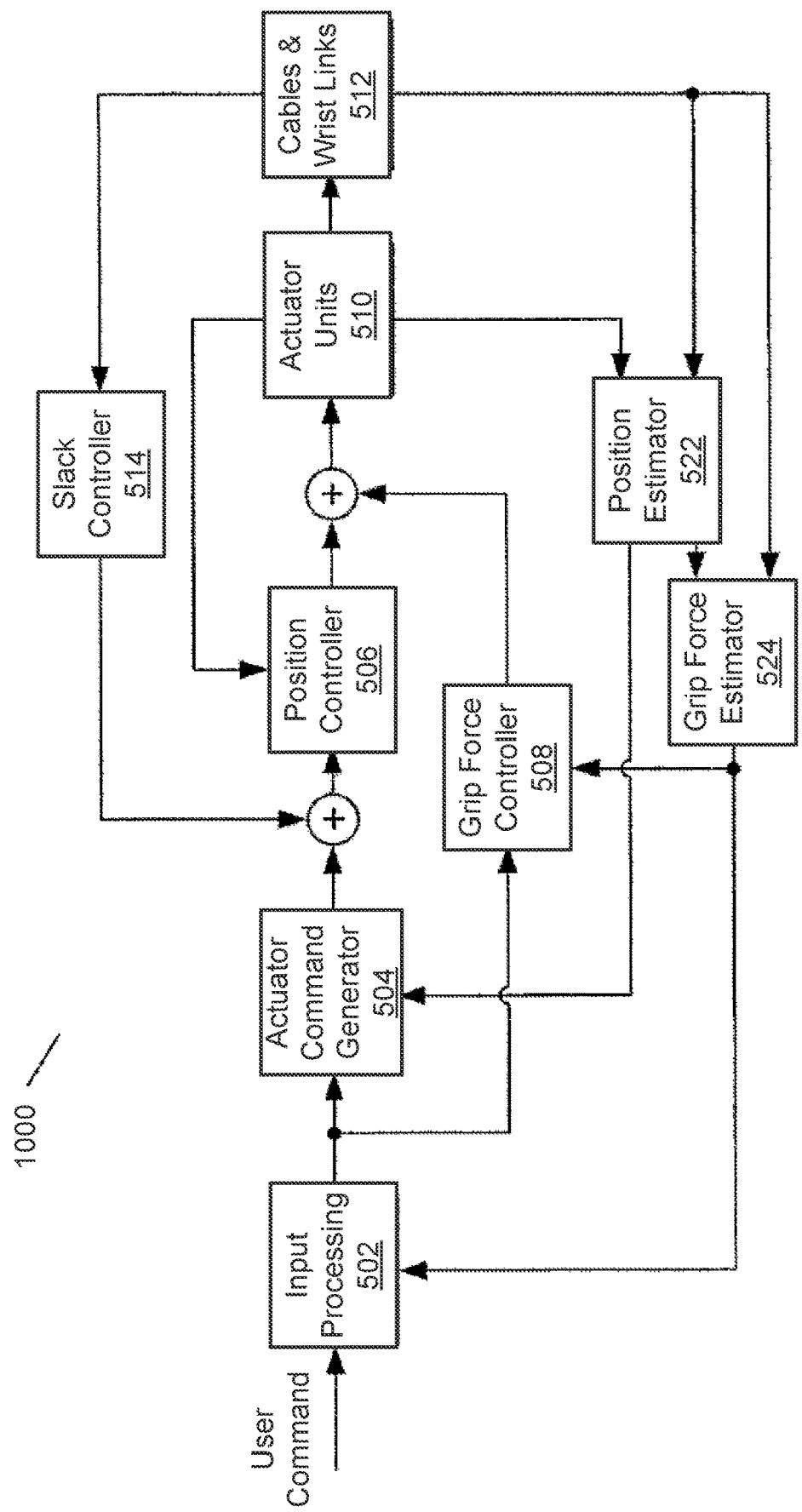
FIG. 10 is a block diagram of an exemplary control system for controlling the position and grip force of an end effector of a robotic surgical tool when the end effector is in the position mode or force mode, or when the end effector transitions between the position mode and the force mode, in accordance with aspects of the subject technology.

FIG. 10 is a block diagram of an exemplary control system 1000 for controlling the position and grip force of an end effector of a robotic surgical tool when the end effector is in the position mode or force mode, or when the end effector transitions between the position mode and the force mode, in accordance with aspects of the subject technology. In one embodiment, the end effector includes wrist jaws. The robotic control system 1000 comprises an input processing unit 502, an actuator command generator 504, a position controller 506, a grip force controller 508, a plant including one or more actuator units 510 and/or cables and wrist links 512, a slack controller 514, a position estimator 522 and a grip force estimator 524.

The input processing unit 502 and the actuator command generator 504 receive desired angular positions of the wrist jaws and translate the desired angular positions into corresponding actuator position commands (via inverse kinematics algorithm), which are output to the position controller 506 and/or grip force controller 508. For example, the input desired angular positions may include the desired $\theta_{jaw}$, desired $\theta_{pitch}$ and desired $\theta_{yaw}$. The desired $\theta_{jaw}$ may be treated as a position command when the desired $\theta_{jaw}$ is greater than or equal to the threshold for detent. When the desired $\theta_{jaw}$ is less than the threshold for detent, the desired $\theta_{jaw}$ may be translated to a desired grip force command (e.g., commanded grip force) by the grip force controller 508, which may generate a current command to achieve the desired grip force.

The position controller 506 may receive position feedback from position and/or speed sensors on the actuator units 510. Achieving the desired actuator positions can in turn lead to the desired position of the wrist jaws due to the kinematic relationship between the actuators and the wrist jaws. Since the actuator units 510 are coupled to the robotic wrist through elastic cables (or wires), which may change length under force, estimation only based on a pure kinematic relation between actuator positions and wrist movements may not be accurate. The position estimator 522 may provide the actuator command generator 504 and the grip force estimator 524 with a more accurate estimate of the wrist joint positions and velocities by taking into account the cable elasticity in estimation algorithms (e.g., using a Kalman filter). The estimated position and velocity information can then be used for accurate positioning of the wrist, as well as estimation of the friction.

In one embodiment, the grip force controller 508 takes feedback of cable tensions measured by load cells or torque sensors on the cable wires. Algorithms can then be used by the grip force estimator 524 to estimate the grip force between the jaws based on the tension values measured on the cables. The grip force controller 508 may compare the estimated value to the desired grip force and generates additional current commands to achieve the desired grip force. The wrist jaws may be coupled to the tool drive through four independent cables, each of which is actuated by an independent motor. In one embodiment, the motors may be driven by current. The current command may include two parts: the first part of the driving current may be from the position controller 506 and the second part from the grip force controller 508. The two current commands may be summed up and sent to the actuator units 510.

The slack controller 514 may perform the task of ensuring the tensions on the cables never fall below zero (or a predetermined positive value to compensate slackness). Cables are tension-only members of the end effector, to which negative forces cannot be applied. Therefore, it is desirable to prevent the tensions on the cables from dropping to zero. To achieve this goal, the slack controller 514 may monitor the force values from load cells on the cables and compare the minimum of the force values to a predetermined threshold. If the minimum force value across all the cables falls below the threshold, the slack controller 514 may generate an additional position command to all the actuators to ensure that the desired minimum tension is maintained.

To smooth the grip force applied during mode transitions, the input processing unit 502 may employ a debouncing technique when detent is set at zero degree. The debouncing technique may determine if the desired $\theta_{jaw}$ is smaller than the threshold for detent for a pre-specified minimum duration before enabling the grip force controller 508 to transition the wrist jaws from the position mode to the force mode. When transitioning from the force mode to the position mode, the input processing unit 502 may disable the grip controller 508 as soon as the desired $\theta_{jaw}$ is greater than or equal to the threshold for detent. Thus, the debouncing technique may be one-sided. The debouncing technique prevents the grip force controller 508 from repeatedly getting enabled and disabled, a condition that may cause oscillation in the commanded grip force when the desired $\theta_{jaw}$ oscillates around detent.

Figure 11A:
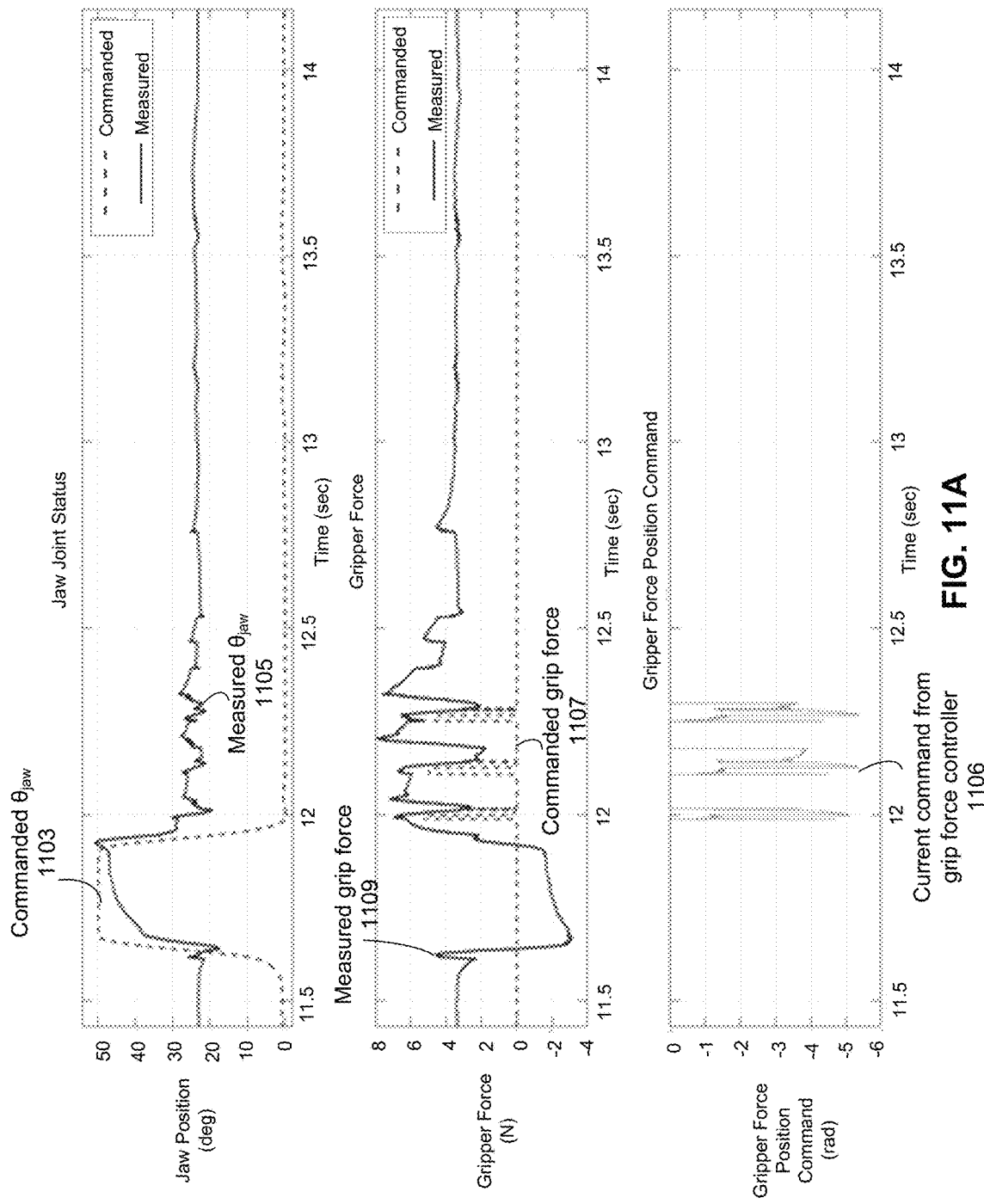
FIG. 11A is a time plot showing the commanded jaw angle, the measured jaw angle, the commanded grip force, the measured grip force of the wrist jaws, and activities of a grip force controller when the jaw angle is set to be around the threshold between the position mode and the force mode without a debouncing algorithm.

FIG. 11A is a time plot showing the commanded $\theta_{jaw}$ 1103, the measured $\theta_{jaw}$ 1105, the commanded grip force 1107, the measured grip force 1109 of the wrist jaws, and the current command 1106 from a grip force controller (e.g., grip force controller 508 of FIG. 10) when the commanded $\theta_{jaw}$ 1103 is set to be around the threshold for detent without a debouncing algorithm. The threshold for detent is set at zero so that when the commanded $\theta_{jaw}$ 1103 is greater than or equal to zero degree, the wrist jaws are operating in the position mode. When the commanded $\theta_{jaw}$ 1103 is less than zero degree, the wrist jaws are operating in the force mode. A positive grip force indicates the grip force in the force mode and a negative grip force indicates the grip force in the position mode.

FIG. 11A shows that between time 11.6 and 12 second, the wrist jaws are operating in the position mode. After time 12 second, the commanded $\theta_{jaw}$ 1103 is set around the threshold for detent due to the user input device (UID) set at detent. The measured $\theta_{jaw}$ 1105 stays above about 20 degrees, presumably because the jaws are grasping an object. The grip force controller 508 is repeatedly enabled and disabled when the wrist jaws teeters between the position mode and the force mode, causing the oscillations in the commanded grip force 1107 and the current command 1106 from the grip force controller 508 when the grip force controller 508 is enabled during the force mode. The result is the undesired large swings in the measured grip force 1109 observed between time 12 and 12.4 second. The measured $\theta_{jaw}$ 1105 also shows some undesired oscillations due to the swings in the measured grip force 1109.

Figure 11B:
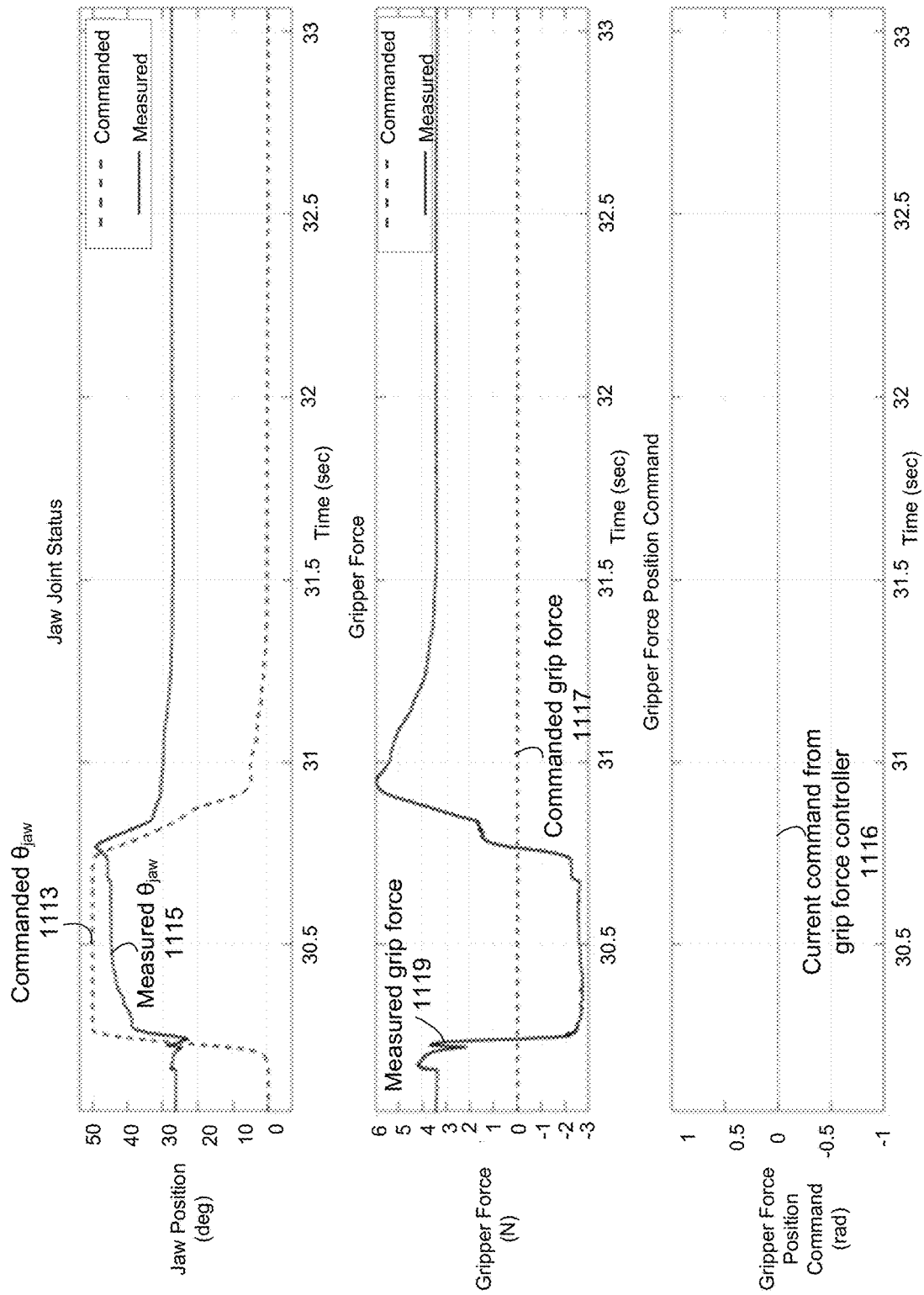
FIG. 11B is a time plot showing the commanded jaw angle, the measured jaw angle, the commanded grip force, the measured grip force of the wrist jaws, and activities of a grip force controller when a control system employs a debouncing algorithm when setting the jaw angle to be around the threshold between the position mode and the force mode, in accordance with aspects of the subject technology.

FIG. 11B is a time plot showing the commanded $\theta_{jaw}$ 1113, the measured $\theta_{jaw}$ 1115, the commanded grip force 1117, the measured grip force 1119 of the wrist jaws, and the current command 1116 from the grip force controller 508 when a control system (e.g., input processing unit 502 and actuator command generator 504 of FIG. 10) employs a debouncing algorithm when the commanded $\theta_{jaw}$ 1113 is set to be around detent, in accordance with aspects of the subject technology. The threshold for detent is again set at zero. Between time 30.2 and 30.9 second, the wrist jaws are operating in the position mode. After time 30.9 second, the commanded $\theta_{jaw}$ 1113 is set around the threshold for detent.

The debouncing algorithm may enable the grip force controller 508 to transition the wrist jaws from the position mode to the force mode only if the desired $\theta_{jaw}$ is less than zero degree for a pre-specified minimum duration. Because the control system does not detect this condition, the wrist jaws remain in the position mode and the grip force controller 508 is not enabled. As a result, the commanded grip force 1117 stays at the default value of 0 N and the current command 1116 from the grip force controller 508 also stays at 0. The measured grip force 1119 exhibits none of the large swings and the measured $\theta_{jaw}$ 1115 exhibits none of the oscillations observed in FIG. 11A, ensuring a smooth application of the grip force (the measured grip force 1119 is shown as positive even though the wrist jaws remain in the position mode).

Smooth applications of the grip force may also become important when the wrist jaws are grasping an object when transitioning between the position mode and the force mode. For example, during the position mode even though the grip force controller 508 is not enabled, there may be non-zero measured grip force if the wrist jaws are grasping an object. When the desired $\theta_{jaw}$ drops below the threshold for detent, indicating a transition from the position mode to the force mode, the grip force controller 508 may initially drive the commanded grip force from 0 N. Similarly, when transitioning from the force mode to the position mode, when the grip force controller 508 is disabled, the commanded grip force may reset to the default value of 0 N output from the position controller 506. As a result, there may be a sudden change in the measured grip force during the transitions, potentially causing the wrist jaws to drop the object.

Figure 12A:
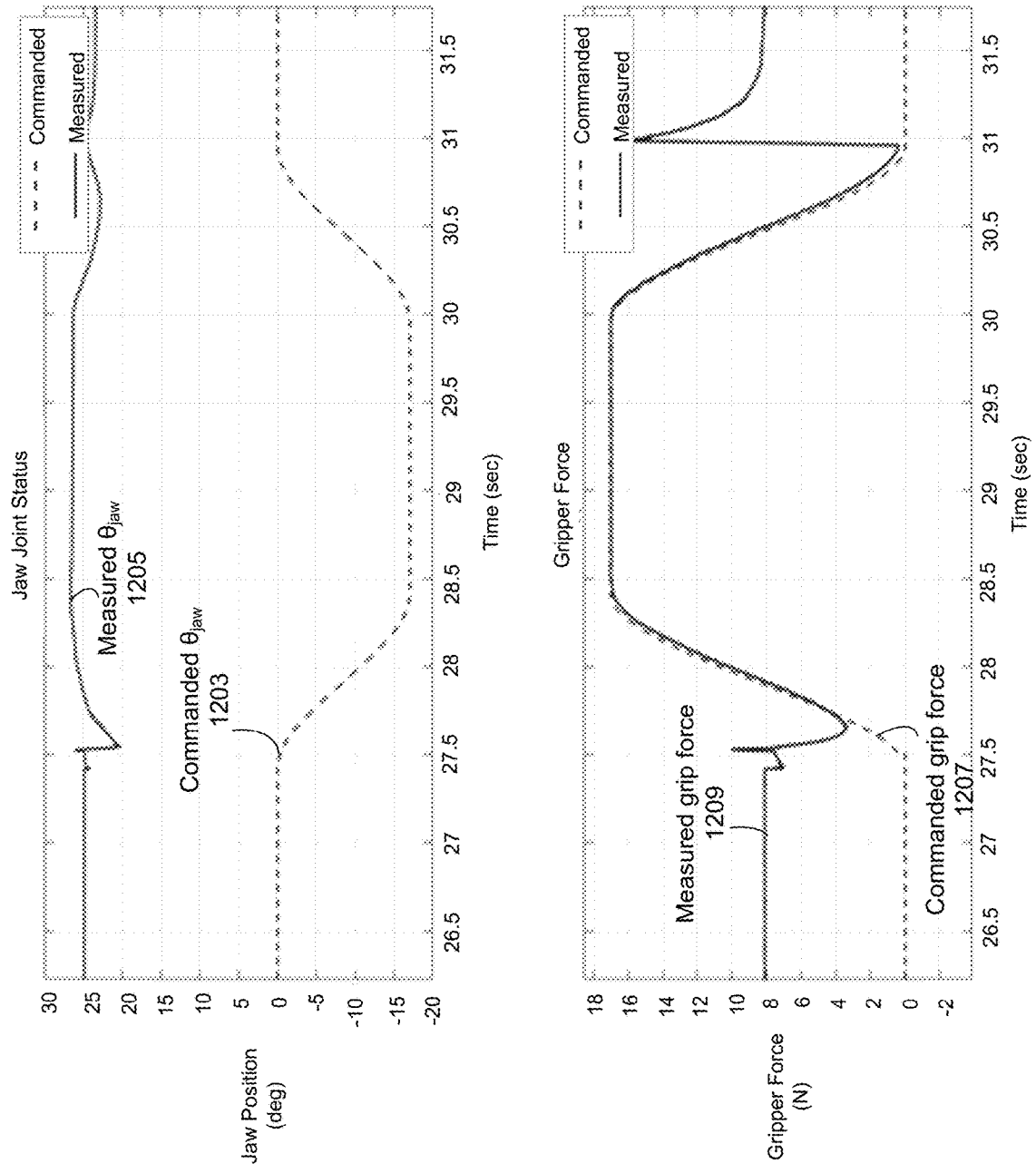
FIG. 12A is a time plot showing the commanded jaw angle, the measured jaw angle, the commanded grip force, and the measured grip force of the wrist jaws when changes in the measured grip force is not constrained when the jaws transition from the position mode to the force mode and back to the position mode.

FIG. 12A is a time plot showing the commanded $\theta_{jaw}$ 1203, the measured $\theta_{jaw}$ 1205, the commanded grip force 1207, and the measured grip force 1209 of the wrist jaws when a control system does not attempt to limit changes in the measured grip force 1209 when the wrist jaws transition from the position mode to the force mode and back to the position mode. The threshold for detent is again set at 0 so that when the commanded $\theta_{jaw}$ 1203 is greater than or equal to 0 degree, the wrist jaws are operating in the position mode. When the commanded $\theta_{jaw}$1203 is less than 0 degree, the wrist jaws are operating in the force mode.

The wrist jaws are initially operating in the position mode. The commanded $\theta_{jaw}$ 1203 is initially at 0 degree and the commanded grip force 1207 is initially at 0 N. The measured $\theta_{jaw}$1205 is at 25 degrees and the measured grip force 1209 is at 8 N due to an object held between the jaws. At time 27.5 second, the commanded $\theta_{jaw}$ 1203 becomes negative to transition the wrist jaws from the position mode to the force mode. When the grip force controller 508 is enabled, the commanded grip force 1207 ramps up from 0 N until the commanded $\theta_{jaw}$ 1203 reaches its most negative value. However, the measured grip force 1209 experiences a sudden drop of 5 N during the transition before ramping up as commanded. At time 30 second, the commanded $\theta_{jaw}$ 1203 starts to become less negative. The commanded grip force 1207 starts to ramp down and the measured grip force 1209 follows as commanded. At time 31 second, the commanded $\theta_{jaw}$ 1203 becomes positive to transition the wrist jaws from the force mode back to the position mode. When the grip force controller 508 is disabled, the measured grip force 1209 experiences a sudden jump from 0 N to the quiescent 8 N of the position mode with some overshoot. It is desired to minimize sudden changes in the measured grip force 1209 during the transitions.

In one embodiment, to minimize sudden changes in the grip force of the wrist jaws when holding an object during the transition from the position mode to the force mode, the grip force controller 508 may adjust the commanded grip force. For example, the grip force controller 508 may set the commanded grip force to be the currently measured grip force minus a pre-specified margin when the grip force controller 508 is enabled upon the commanded $\theta_{jaw}$ becoming less than the threshold for detent and if certain conditions are satisfied. Doing so may prevent the measured grip force from dropping to a value close to 0 N during the transition, thereby reducing the probability of the jaws dropping the object held between the jaws. In one embodiment, the measured grip force may be generated by the grip force estimator 524 based on the tension values measured on the cables from cable and wrist links 512.

To evaluate a first condition for adjusting the commanded grip force, the grip force controller 508 may determine if the commanded grip force is or will be increasing due to the grip force controller 508 getting enabled as indicated by the commanded $\theta_{jaw}$ decreasing below the threshold for detent. For a second condition, the grip force controller 508 may determine if the error between the measured grip force and the commanded grip force is larger than a pre-specified maximum force error. In one embodiment, the grip force controller 528 may use a debouncing technique for one or both of the conditions. If these two conditions are satisfied, the grip force controller 508 may set the commanded grip force to be the currently measured grip force minus the pre-specified margin.

In one embodiment, to minimize sudden changes in the grip force of the wrist jaws when holding an object during the transition from the force mode to the position mode, the grip force controller 508 may adjust the commanded grip force. For example, the grip force controller 508 may set the commanded grip force to a pre-specified minimum grip force value when the grip force controller 508 is disabled upon the commanded $\theta_{jaw}$ becoming more than the threshold for detent and if certain conditions are satisfied. Doing so instead of starting from the default 0 N of the position mode may reduce the change for the measured grip force to rise to the quiescent grip force of the position mode.

To evaluate the conditions for adjusting the grip force, the grip force controller 508 may determine if the commanded grip force is smaller than the pre-specified minimum grip force value. The grip force controller 508 may also determine if the commanded grip force is decreasing as indicated by the commanded $\theta_{jaw}$ increasing toward or crossing the threshold for detent. The grip force controller 508 may additionally determine if the absolute value of the error between the measured grip force and the minimum grip force value is smaller than a pre-specified maximum grip force error value. In one embodiment, the grip force controller 528 may use a debouncing technique for one or more of the conditions. If all the conditions are satisfied, the grip force controller 508 may set the commanded grip force to be the pre-specified minimum grip force value. In one embodiment, the pre-specified minimum grip force value may be set to 3 N.

Figure 12B:
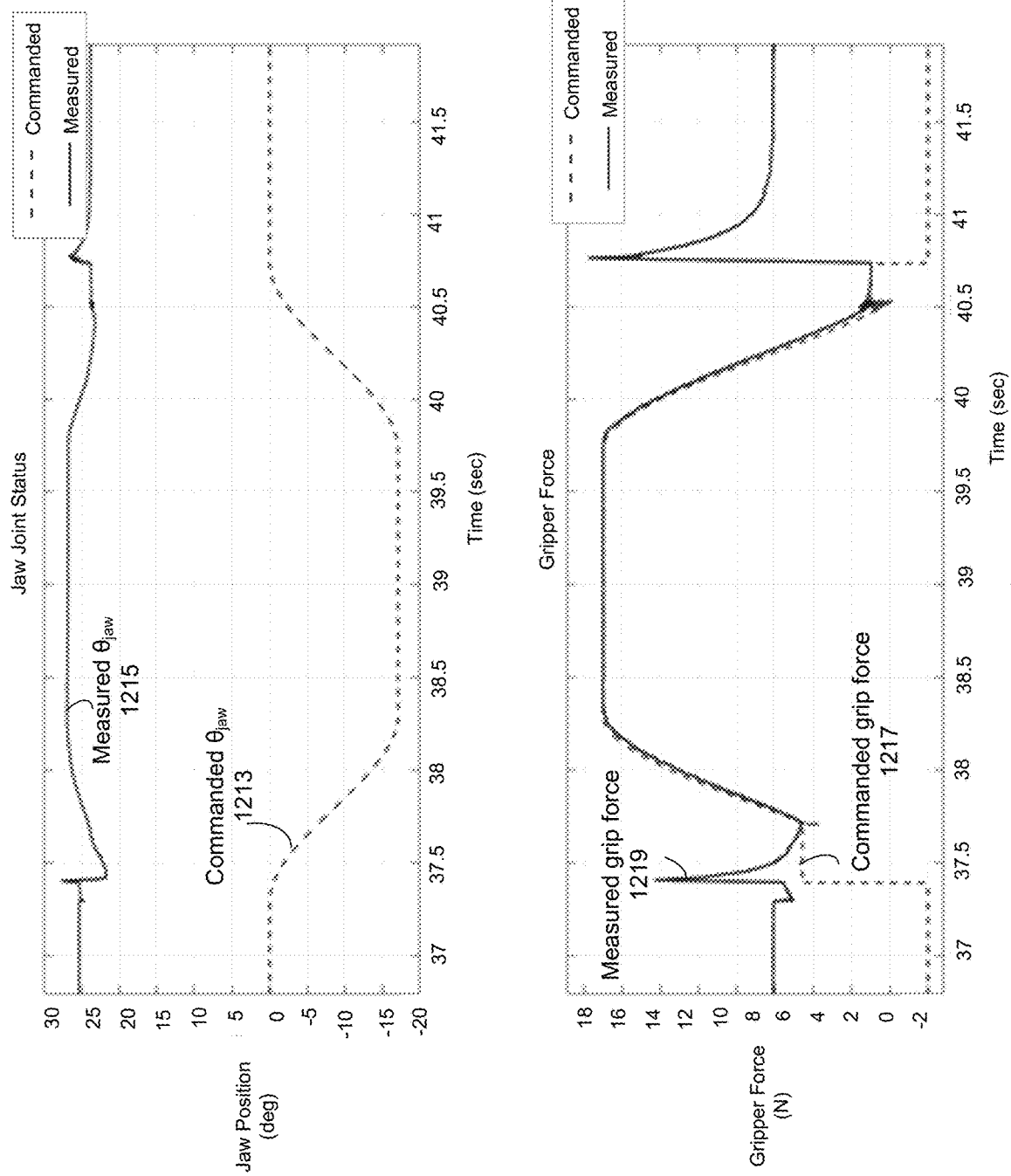
FIG. 12B is a time plot showing the commanded jaw angle, the measured jaw angle, the commanded grip force, and the measured grip force of the wrist jaws when a control system constrains changes in the grip force as the jaws transition between the position mode and the force mode, in accordance with aspects of the subject technology.

FIG. 12B is a time plot showing the commanded $\theta_{jaw}$ 1213, the measured $\theta_{jaw}$ 1215, the commanded grip force 1217, and the measured grip force 1219 of the wrist jaws when a control system limits changes in the measured grip force 1219 as the wrist jaws transition between the position mode and the force mode, in accordance with aspects of the subject technology. The threshold for detent is again set at 0 so that when the commanded $\theta_{jaw}$ 1213 is greater than or equal to 0 degree, the wrist jaws are operating in the position mode. When the commanded $\theta_{jaw}$1213 is less than 0 degree, the wrist jaws are operating in the force mode. The pre-specified maximum grip force error value, which is not to be exceeded by the absolute value of the error between the measured grip force and the commanded grip force, is set to more than 8 N. The pre-specified minimum grip force value is set to 3 N.

The wrist jaws are initially operating in the position mode with the initial states of the commanded $\theta_{jaw}$ 1213, measured $\theta_{jaw}$ 1215, commanded grip force 1217, and measured grip force 1219 the same as in FIG. 12A. At time 37.4 second, the commanded $\theta_{jaw}$ 1203 becomes negative to transition the wrist jaws from the position mode to the force mode. However, instead of starting from 0 N in the force mode, the commanded grip force 1217 starts from about 6.2 N, obtained by subtracting a pre-specified margin from the measured grip force 1219 at this time. The conditions for the adjustment to the commanded grip force 1217 are satisfied because the absolute value of the error between the measured grip force 1219 and the commanded grip force 1217 is smaller than the pre-specified maximum force error. The result is that the measured grip force 1219 experiences a significantly smaller drop than without the adjustment to the commanded grip force 1217 during the transition from the position mode to the force mode. The commanded grip force 1217 stays at 6.2 N until the commanded grip force 1217 as determined from the increasingly negative commanded $\theta_{jaw}$ 1213 becomes greater than 6.2 N.

At time 39.8 second, the commanded $\theta_{jaw}$ 1213 starts to become less negative. The commanded grip force 1217 starts to ramp down and the measured grip force 1219 follows as commanded. At time 40.5 second, the commanded grip force 1217 stays at the pre-specified minimum grip force value of 3 N instead of continuing to ramp down to 0 N as otherwise would have occurred without the adjustment as the commanded $\theta_{jaw}$ 1213 becomes positive to transition the wrist jaws from the force mode to the position mode. The conditions for the adjustment to the commanded grip force 1217 are satisfied because the measured grip force 1219 is smaller than the pre-specified minimum grip force value of 3 N and the absolute value of the error between the measured grip force 1219 and the commanded grip force 1217 is smaller than the pre-specified maximum force error. The result is that the measured grip force 1219 experiences a significantly smaller change than without the adjustment to the commanded grip force 1217 as the measured grip force 1219 jumps to the quiescent 8 N of the position mode during the transition. The commanded grip force 1217 stays at 3 N until the commanded grip force 1217 as determined from the commanded $\theta_{jaw}$ 1213 becomes 0 N.

Figure 13:
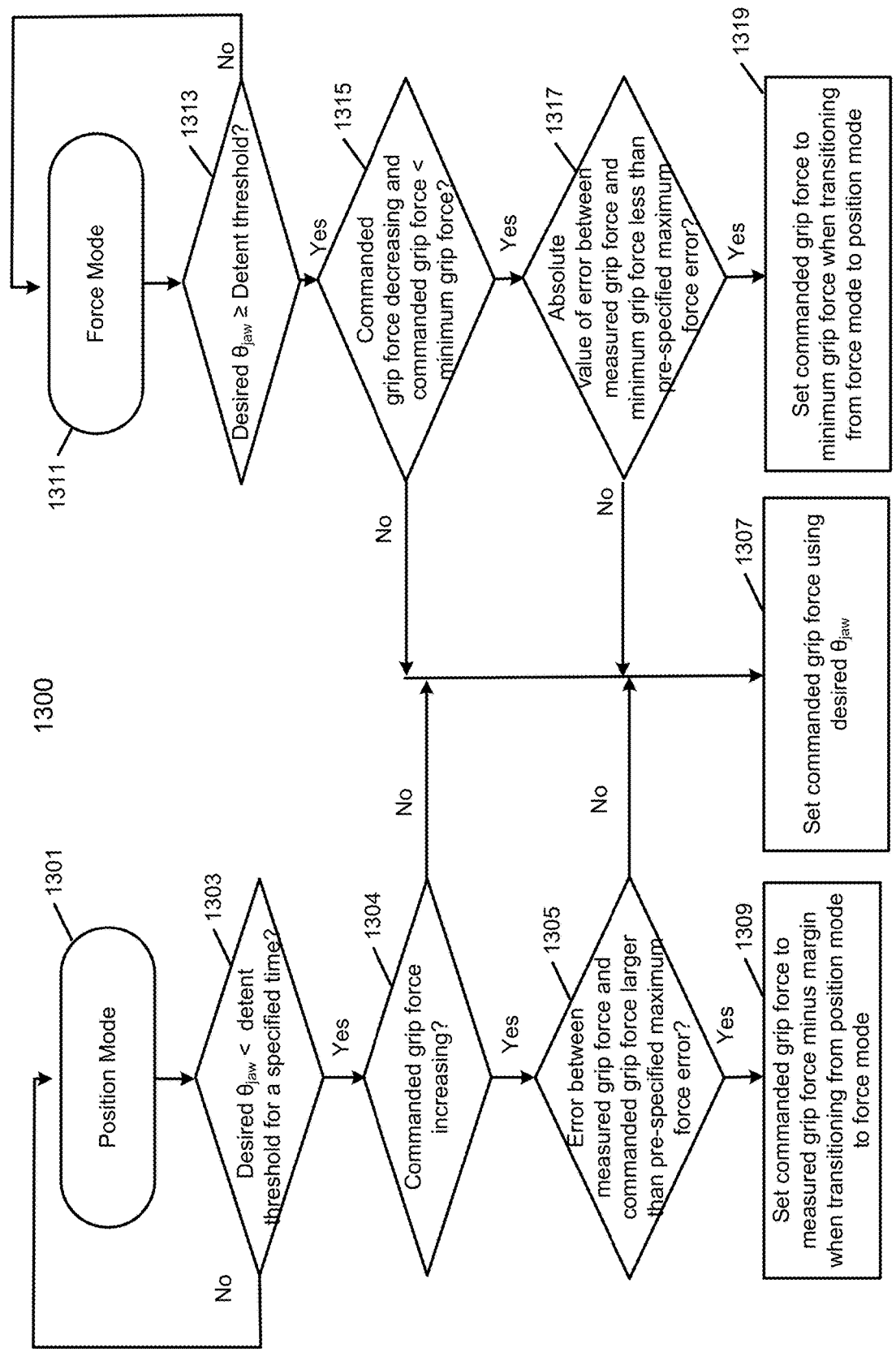
FIG. 13 is a flow chart illustrating a method for a feedback control of a surgical robotic system to employ a debouncing algorithm when setting the desired jaw angle of the wrist jaws around the threshold between the position mode and the force mode, or to adjust the commanded grip force to limit changes in the measured grip force when the jaws transition between the position mode and the force mode, in accordance with aspects of the subject technology.

FIG. 13 is a flow chart illustrating a method 1300 for a feedback control of a surgical robotic system to employ a debouncing algorithm when setting the desired $\theta_{jaw}$ of the wrist jaws around the threshold for detent, or to adjust the commanded grip force to limit changes in the measured grip force when the wrist jaws transition between the position mode and the force mode, in accordance with aspects of the subject technology. The method 1300 may be implemented by the controller 562 of the control system of FIG. 5 or the grip force controller 508 of the control system of FIG. 10 that receives the desired $\theta_{jaw}$ from user input and the measured grip force from sensors and estimators 566 of FIG. 5 or the grip force estimator 524 of FIG. 10, respectively, to generate commanded grip force for driving the wrist jaws.

Starting from the position mode in block 1301, the method 1300 determines if the desired $\theta_{jaw}$ is smaller than the threshold for detent for a minimum duration in block 1303. In one embodiment, the minimum duration may be pre-specified or may be configurable. Block 1303 implements a debouncing algorithm to prevent the force mode from repeatedly being enabled and disabled, a condition that may cause oscillation in the commanded grip force when the desired $\theta_{jaw}$ is set around the threshold for detent. In one embodiment, block 1303 may determine if the commanded grip force is or will be increasing as indicated by the desired $\theta_{jaw}$ decreasing below the threshold for detent. If the desired $\theta_{jaw}$ is not smaller than the threshold for detent for the pre-specified minimum duration, the wrist jaws remain in the position mode of block 1301.

Otherwise, if the desired $\theta_{jaw}$ is smaller than the threshold for detent for the pre-specified minimum duration, the wrist jaws are transitioning from the position mode to the force mode. Block 1304 determines if the commanded grip force is increasing. If this condition is false, block 1307 sets the commanded grip force as translated from the desired $\theta_{jaw}$ and the commanded grip force is not adjusted to limit changes in the measured grip force during the mode transition. Otherwise, if the condition in block 1304 is true, block 1305 determines if the error between the measured grip force and the commanded grip force is larger than a maximum force error during the mode transition. The commanded grip force may be at the default 0 N in the position mode prior to the mode transition. The measured grip force may be different from the commanded grip force prior to the mode transition because the wrist jaws may be grasping an object. In one embodiment, the maximum force error may be pre-specified or may be configurable.

If the condition in block 1305 is true, block 1309 sets the commanded grip force to the measured grip force minus a margin when the wrist jaws transition from the position mode to the force mode. In one embodiment, the margin may be pre-specified or may be configurable. Otherwise, if the condition in block 1305 is false, block 1307 sets the commanded grip force as translated from the desired $\theta_{jaw}$ and the commanded grip force is not adjusted to limit changes in the measured grip force during the mode transition.

When the wrist jaws are in the force mode in block 1311, the method 1300 determines if the desired $\theta_{jaw}$ is greater than or equal to the threshold for detent in block 1313. In one embodiment, block 1311 may determine if the commanded grip force is decreasing as indicated by the desired $\theta_{jaw}$ increasing toward the threshold for detent and that the desired $\theta_{jaw}$ is just below the threshold for detent. If the desired $\theta_{jaw}$ is not greater than or equal to the threshold for detent, the wrist jaws remain in the force mode of block 1311.

Otherwise, if the desired $\theta_{jaw}$ is greater than or equal to the threshold for detent, the wrist jaws are transitioning from the force mode to the position mode. Block 1315 determines if the commanded grip force is decreasing and if the commanded grip force is less than a minimum grip force during the mode transition. In one embodiment, the minimum grip force may be pre-specified or may be configurable. If the commanded grip force is not decreasing or if the commanded grip force is not less than the minimum grip force during the mode transition, block 1307 sets the commanded grip force as translated from the desired $\theta_{jaw}$ and the commanded grip force is not adjusted to limit changes in the measured grip force during the mode transition.

Otherwise, if the commanded grip force is decreasing and if the commanded grip force is less than the minimum grip force during the mode transition, block 1317 determines if the absolute value of the error between the measured grip force and the minimum grip force value is smaller than a maximum force error during the mode transition. In one embodiment, the maximum force error may be pre-specified or may be configurable. The maximum force error in block 1317 for the force-to-position mode transition may be the same or different from the maximum force error in block 1305 for the position-to-force mode transition.

If the condition in block 1317 is true, block 1319 sets the commanded grip force to the minimum grip force when the wrist jaws transition from the force mode to the position mode. Otherwise, if the condition in block 1317 is false, block 1307 sets the commanded grip force as translated from the desired $\theta_{jaw}$ and the commanded grip force is not adjusted to limit changes in the measured grip force during the mode transition.

Figure 14:
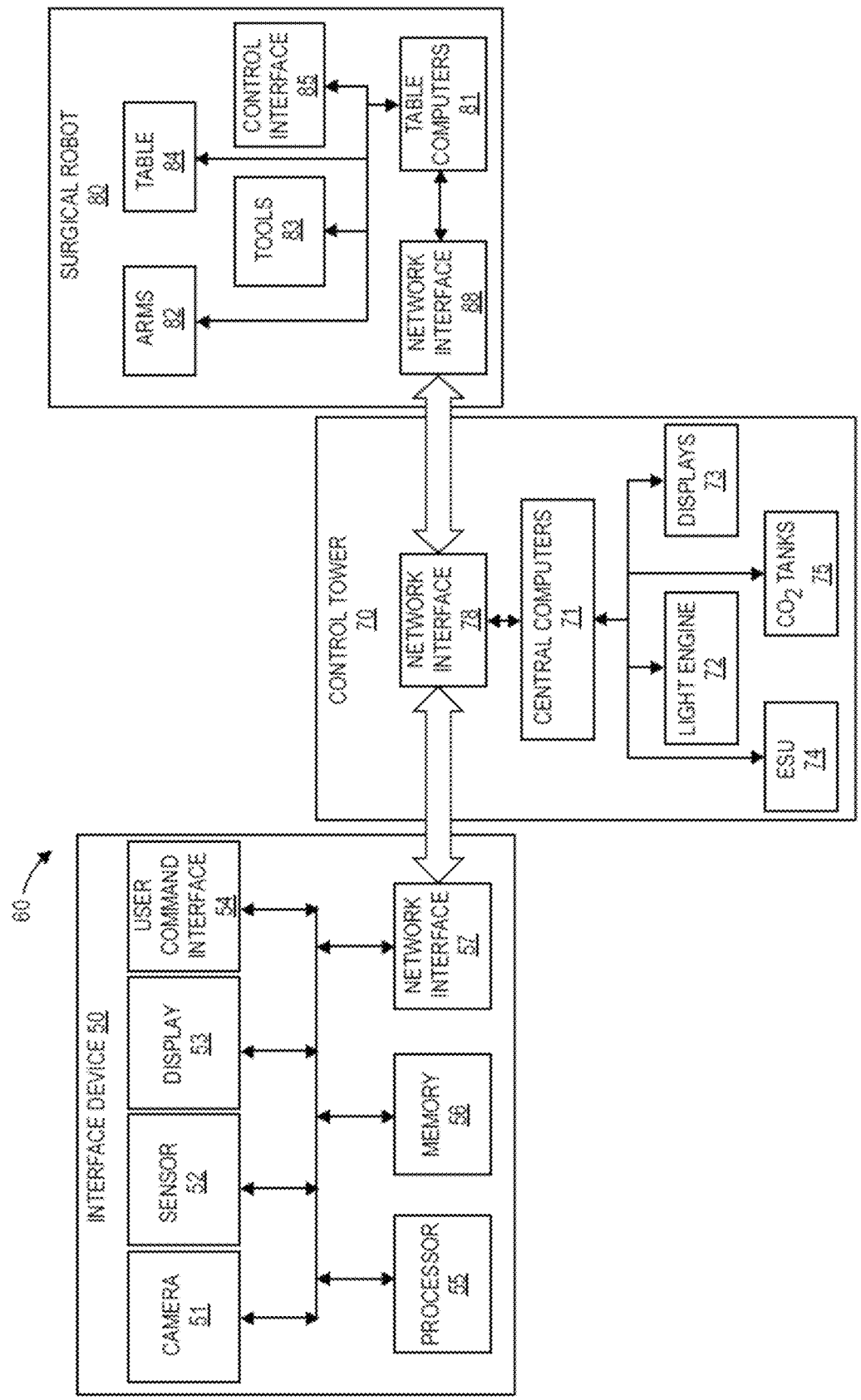
FIG. 14 is a block diagram illustrating exemplary hardware components of a surgical robotic system, in accordance with aspects of the subject technology.

FIG. 14 is a block diagram illustrating exemplary hardware components of a surgical robotic system, in accordance with aspects of the subject technology. The surgical robotic system may include an interface device 50, a surgical robot 80, and a control tower 70. The surgical robotic system may include other or additional hardware components; thus, the diagram is provided by way of example and not a limitation to the system architecture.

The interface device 50 includes a camera 51, sensor 52, display 53, user command interface 54, processor 55, memory 56, and network interface 57. The camera 51 and the sensor 52 may be configured to capture color images and depth-image information of the surgical robotic system. Images captured by the camera 51 and sensor 52 may be projected on the display 53. The processor 55 may be configured to run an operating system to control the operation of the interface device 50. The memory 56 may store the image processing algorithms, operating system, program codes, and other data memories used by the processor 55. The interface device 50 may be used to generate the desired $\theta_{pitch}$, $\theta_{yaw}$, and $\theta_{jaw}$ of the wrist jaws under the control of a remote operator.

The user command interface 54 may include the interface for other features such as the Web portal. The hardware components may communicate via a bus. The interface device may use the network interface 57 to communicate with the surgical robotic system through an external interface. The external interface may be a wireless or a wired interface.

The control tower 70 may be a mobile point-of-care cart housing touchscreen displays, computers that control the surgeon's robotically-assisted manipulation of instruments, safety systems, graphical user interface (GUI), light source, and video and graphics computers. The control tower 70 may comprise central computers 71 that may include at least a visualization computer, a control computer, and an auxiliary computer, various displays 73 that may include a team display and a nurse display, and a network interface 78 coupling the control tower 70 to both the interface device 50 and the surgical robot 80. The control tower 70 may also house third-party devices, such as an advanced light engine 72, an electrosurgical generator unit (ESU) 74, and insufflator and $CO_2$ tanks 75. The control tower 70 may offer additional features for user convenience, such as the nurse display touchscreen, soft power and E-hold buttons, user-facing USB for video and still images, and electronic caster control interface. The auxiliary computer may also run a real-time Linux, providing logging/monitoring and interacting with cloud-based web services. The central computers 71 of the control tower 70 may receive the desired $\theta_{pitch}$, $\theta_{yaw}$, and $\theta_{jaw}$ of the wrist jaws generated by the interface device 50 to implement the methods described herein for controlling the grip force or opening force of the jaws.

The surgical robot 80 comprises an articulated operating table 84 with a plurality of integrated arms 82 that may be positioned over the target patient anatomy. A suite of compatible tools 83 may be attached to or detached from the distal ends of the arms 82, enabling the surgeon to perform various surgical procedures. The surgical robot 80 may also comprise control interface 85 for manual control of the arms 82, operating table 84, and tools 83. The control interface 85 may include items such as, but not limited to, remote controls, buttons, panels, and touchscreens. Other accessories such as trocars (sleeves, seal cartridge, and obturators) and drapes may also be manipulated to perform procedures with the system. In one embodiment, the plurality of the arms 82 may include four arms mounted on both sides of the operating table 84, with two arms on each side. For certain surgical procedures, an arm mounted on one side of the operating table 84 may be positioned on the other side of the operating table 84 by stretching out and crossing over under the operating table 84 and arms mounted on the other side, resulting in a total of three arms positioned on the same side of the operating table 84. The surgical tool may also comprise table computers 81 and a network interface 88, which may place the surgical robot 80 in communication with the control tower 70.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications. They thereby enable others skilled in the art to best utilize the invention and various embodiments with various modifications as are suited to the particular use contemplated. It is intended that the following claims and their equivalents define the scope of the invention.

The methods, devices, processing, and logic described above may be implemented in many different ways and in many different combinations of hardware and software. The controllers and estimators may comprise electronic circuitry. For example, all or parts of the implementations may be circuitry that includes an instruction processor, such as a Central Processing Unit (CPU), microcontroller, or a microprocessor; an Application Specific Integrated Circuit (ASIC), Programmable Logic Device (PLD), or Field Programmable Gate Array (FPGA); or circuitry that includes discrete logic or other circuit components, including analog circuit components, digital circuit components or both; or any combination thereof. The circuitry may include discrete interconnected hardware components and/or may be combined on a single integrated circuit die, distributed among multiple integrated circuit dies, or implemented in a Multiple Chip Module (MCM) of multiple integrated circuit dies in a common package, as examples.

The circuitry may further include or access instructions for execution by the circuitry. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed as circuitry among multiple system components, such as among multiple processors and memories, optionally including multiple distributed processing systems. Parameters, databases, and other data structures may be separately stored and managed, may be incorporated into a single memory or database, may be logically and physically organized in many different ways, and may be implemented in many different ways, including as data structures such as linked lists, hash tables, arrays, records, objects, or implicit storage mechanisms. Programs may be parts (e.g., subroutines) of a single program, separate programs, distributed across several memories and processors, or implemented in many different ways, such as in a library, such as a shared library (e.g., a Dynamic Link Library (DLL)). The DLL, for example, may store instructions that perform any of the processing described above or illustrated in the drawings, when executed by the circuitry.

Also, the various controllers discussed herein can take the form of processing circuitry, a microprocessor or processor, and a computer-readable medium that stores computer-readable program code (e.g., firmware) executable by the (micro)processor, logic gates, switches, an application specific integrated circuit (ASIC), a programmable logic controller, and an embedded microcontroller, for example. The controller can be configured with hardware and/or firmware to perform the various functions described below and shown in the flow diagrams. Also, some of the components shown as being internal to the controller can also be stored external to the controller, and other components can be used.

What is claimed is:

1. A method for controlling grip force generated by jaws of a gripper tool of a surgical robotic system, comprising:
   receiving, by a processor, an input jaw angle;
   determining, by the processor, based on changes of the input jaw angle relative to a threshold jaw angle that the jaws are transitioning between a position mode and a force mode, the position mode being characterized by positioning an angle of the jaws at the input jaw angle, and the force mode being characterized by driving a grip force of the jaws to a commanded grip force, wherein the commanded grip force is determined based on the input jaw angle being below the threshold jaw angle;
   measuring the grip force between the jaws to generate a measured grip force;
   determining, by the processor, based on the commanded grip force and the measured grip force whether to adjust the commanded grip force during the transitioning between the position mode and the force mode; and
   adjusting, by the processor, the commanded grip force during the transitioning between the position mode and the force mode in response to determining to adjust the commanded grip force.

2. The method of claim 1, wherein determining that the jaws are transitioning between the position mode and the force mode comprises:
   determining that the jaws are transitioning from the position mode to the force mode when the input jaw angle is initially larger than or equal to zero and becomes smaller than zero for a minimum time duration; or
   determining that the jaws are transitioning from the force mode to the position mode when the input jaw angle is initially smaller than zero and becomes larger than or equal to zero.

3. The method of claim 1, wherein determining that the jaws are transitioning between the position mode and the force mode comprises:
   determining, by the processor, that the jaws are initially in the position mode when the input jaw angle is greater than or equal to the threshold jaw angle, wherein the threshold jaw angle is when the jaws simultaneously contact an object when the object is being held between the jaws or when the jaws begin to touch each other when there is no object being held; and
   determining, by the processor, that the jaws transition from the position mode to the force mode when the input jaw angle becomes less than the threshold jaw angle for more than a minimum time duration.

4. The method of claim 3, wherein determining whether to adjust the commanded grip force during the transitioning comprises:
   determining, by the processor, to adjust the commanded grip force when the commanded grip force is increasing and a difference between the measured grip force and the commanded grip force is larger than a maximum grip force error during the transitioning from the position mode to the force mode.

5. The method of claim 4, wherein adjusting the commanded grip force comprises:
   setting, by the processor, the commanded grip force to the measured grip force minus a margin in response to determining to adjust the commanded grip force; or
   setting, by the processor, the commanded grip force based on the input jaw angle in the force mode.

6. The method of claim 1, wherein determining that the jaws are transitioning between the position mode and the force mode comprises:
   determining, by the processor, that the jaws are initially in the force mode when the input jaw angle is smaller than the threshold jaw angle, wherein the threshold jaw angle is when the jaws simultaneously contact an object when the object is being held between the jaws or when the jaws begin to touch each other when there is no object being held; and
   determining, by the processor, that jaws transition from the force mode to the position mode when the input jaw angle becomes larger than or equal to the threshold jaw angle.

7. The method of claim 6, wherein determining whether to adjust the commanded grip force during the transitioning comprises:
   determining, by the processor, to adjust the commanded grip force when the commanded grip force is decreasing, the commanded grip force is less than a minimum grip force, and an absolute value of a difference between the measured grip force and the minimum grip force is less than a maximum grip force error during the transitioning from the force mode to the position mode.

8. The method of claim 7, wherein adjusting the commanded grip force comprises:
   setting, by the processor, the commanded grip force to the minimum grip force in response to determining to adjust the commanded grip force; or
   setting, by the processor, the commanded grip force based on the input jaw angle otherwise.

9. The method of claim 1, further comprising:
   changing, by the processor, the commanded grip force to be based on the input jaw angle in the force mode following the transitioning from the position mode to the force mode when the commanded grip force is adjusted; or
   changing, by the processor, the commanded grip force to be based on the input jaw angle in the position mode following the transitioning from the force mode to the position mode when the commanded grip force is adjusted.

10. An apparatus to control jaws of a gripper tool of a surgical robotic system, comprising:
    a sensor configured to estimate a grip force between the jaws to generate a measured grip force;
    a processor configured to:
    receive a desired jaw angle;
    determine that a control mode for operating the jaws is to transition between a position mode and a force mode based on changes of the desired jaw angle with respect to a threshold jaw angle, the position mode being characterized by positioning an angle between the jaws at the desired jaw angle, and the force mode being characterized by driving a grip force of the jaws to a commanded grip force, wherein the commanded grip force is determined based on the desired jaw angle being below the threshold jaw angle;
    determine whether to adjust the commanded grip force during the transition between the position mode and the force mode based on the commanded grip force and the measured grip force; and
    adjust the commanded grip force during the transition between the position mode and the force mode in response to the determination to adjust the commanded grip force.

11. The apparatus of claim 10, wherein the processor configured to determine that the jaws transition between the position mode and the force mode comprises:
    determine that the jaws transition from the position mode to the force mode when the desired jaw angle is initially larger than or equal to zero and becomes smaller than zero for a minimum time duration; or
    determine that the jaws transition from the force mode to the position mode when the desired jaw angle is initially smaller than zero and becomes larger than or equal to zero.

12. The apparatus of claim 10, wherein the processor configured to determine that the jaws transition between the position mode and the force mode comprises:
    determine that the jaws are initially in the position mode when the desired jaw angle is greater than or equal to the threshold jaw angle, wherein the threshold jaw angle is when the jaws simultaneously contact an object when the object is being held between the jaws or when the jaws begin to touch each other when there is no object being held; and
    determine that the jaws transition from the position mode to the force mode when the desired jaw angle becomes less than the threshold jaw angle for more than a minimum time duration.

13. The apparatus of claim 12, wherein the processor configured to determine whether to adjust the commanded grip force during the transition comprises:
    determine to adjust the commanded grip force when the commanded grip force is increasing and a difference between the measured grip force and the commanded grip force is larger than a maximum grip force error during the transition from the position mode to the force mode.

14. The apparatus of claim 13, wherein the processor configured to adjust the commanded grip force comprises:
    set the commanded grip force to the measured grip force minus a margin in response to the determination to adjust the commanded grip force; or
    set the commanded grip force based on the desired jaw angle in the force mode otherwise.

15. The apparatus of claim 10, wherein the processor configured to determine that the jaws transition between the position mode and the force mode comprises:
    determine that the jaws are initially in the force mode when the desired jaw angle is smaller than the threshold jaw angle, wherein the threshold jaw angle is when the jaws simultaneously contact an object when the object is being held between the jaws or when the jaws begin to touch each other when there is no object being held; and
    determine that the jaws transition from the force mode to the position mode when the desired jaw angle becomes larger than or equal to the threshold jaw angle.

16. The apparatus of claim 15, wherein the processor configured to determine whether to adjust the commanded grip force during the transition comprises:
    determine to adjust the commanded grip force when the commanded grip force is decreasing, the commanded grip force is less than a minimum grip force, and an absolute value of a difference between the measured grip force and the minimum grip force is less than a maximum grip force error during the transition from the force mode to the position mode.

17. The apparatus of claim 16, wherein the processor configured to adjust the commanded grip force comprises:
    set the commanded grip force to the minimum grip force in response to the determination to adjust the commanded grip force; or
    set the commanded grip force based on the desired jaw angle in the force mode otherwise.

18. The apparatus of claim 10, where the processor is further configured to:
    change the commanded grip force to be based on the desired jaw angle in the force mode subsequent to the transition from the position mode to the force mode when the processor is configured to adjust the commanded grip force; or
    change the commanded grip force to be based on the desired jaw angle in the position mode subsequent to the transition from the force mode to the position mode when the processor is configured to adjust the commanded grip force.

19. A surgical robotic system, comprising:
    an end effector including a pair of jaws;
    a user interface device configured to generate an input jaw angle for the jaws;
    a processor communicatively coupled to the end effector, the processor configured to:
    determine that the jaws transition between a position mode and a force mode based on changes of the input jaw angle with respect to a threshold jaw angle, the position mode being characterized by positioning an angle between the jaws at the input jaw angle, and the force mode being characterized by driving a grip force of the jaws to a commanded grip force wherein the commanded grip force is determined based on the input jaw angle being below the threshold jaw angle;
    measure a grip force between the pair of jaws to generate a measured grip force;
    determine whether to adjust the commanded grip force during the transition between the position mode and the force mode based on the commanded grip force and the measured grip force; and
    adjust the commanded grip force during the transition between the position mode and the force mode in response to the determination to adjust the commanded grip force.

20. The surgical robotic system of claim 19, wherein the processor configured to determine that the jaws transition between the position mode and the force mode comprises:
    determine that the jaws are initially in the position mode when the input jaw angle is greater than or equal to the threshold jaw angle, wherein the threshold jaw angle is when the jaws simultaneously contact an object when the object is being held between the jaws or when the jaws begin to touch each other when there is no object being held; and
    determine that that the jaws transition from the position mode to the force mode when the input jaw angle becomes less than the threshold jaw angle for more than a minimum time duration,
    and wherein the processor configured to determine whether to adjust the commanded grip force during the transition comprises:
    determine to adjust the commanded grip force when the commanded grip force is increasing and a difference between the measured grip force and the commanded grip force is larger than a maximum grip force error during the transition from the position mode to the force mode,
    and wherein the processor configured to adjust the commanded grip force comprises:

set the commanded grip force to the measured grip force minus a margin in response to the determination to adjust the commanded grip force; or set the commanded grip force based on the input jaw angle in the force mode otherwise.

\* \* \* \* \*